United States Patent
Fisk

(10) Patent No.: US 9,664,626 B2
(45) Date of Patent: May 30, 2017

(54) COATING INSPECTION METHOD

(71) Applicant: SIO2 MEDICAL PRODUCTS, INC., Auburn, AL (US)

(72) Inventor: Thomas E. Fisk, Green Valley, AZ (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 180 days.

(21) Appl. No.: 14/440,277

(22) PCT Filed: Oct. 31, 2013

(86) PCT No.: PCT/US2013/067852
§ 371 (c)(1),
(2) Date: May 1, 2015

(87) PCT Pub. No.: WO2014/071061
PCT Pub. Date: May 8, 2014

(65) Prior Publication Data
US 2015/0293031 A1    Oct. 15, 2015

Related U.S. Application Data

(60) Provisional application No. 61/721,092, filed on Nov. 1, 2012.

(51) Int. Cl.
*G01N 21/55* (2014.01)
*G01N 21/90* (2006.01)
(Continued)

(52) U.S. Cl.
CPC ......... *G01N 21/9072* (2013.01); *C23C 16/04* (2013.01); *C23C 16/50* (2013.01);
(Continued)

(58) Field of Classification Search
CPC ......... C23C 16/04; C23C 16/50; C23C 16/52; G01B 11/0625; G01N 21/9072; G01N 21/9081
(Continued)

(56) References Cited

U.S. PATENT DOCUMENTS 3,274,267 A   9/1966   Chow
3,297,465 A   1/1967   Connell
(Continued)

FOREIGN PATENT DOCUMENTS

AT    414209 B    10/2006
AT    504533 A1    6/2008
(Continued)

OTHER PUBLICATIONS

US 5,645,643, 07/1997, Thomas (withdrawn)
(Continued)

*Primary Examiner* — Tri T Ton
(74) *Attorney, Agent, or Firm* — McAndrews, Held & Malloy, Ltd.

(57) ABSTRACT

A reflectometry method and other methods for detecting discontinuities in a chemical vapor deposition (CVD) coating are disclosed. The method includes several steps. A thermoplastic vessel wall (710) is provided having an outside surface, an inside surface, and a CVD coating on at least one of the inside and outside surfaces. The vessel wall and the CVD coating have different indices of refraction. Electromagnetic energy (718) is impinged on multiple positions of the CVD coating under conditions effective to cause energy to reflect from the multiple positions of the CVD coating. The reflected energy is analyzed to determine whether the reflected energy includes at least one artifact of a discontinuity in the CVD coating.

15 Claims, 18 Drawing Sheets

(51) Int. Cl.
  *C23C 16/04* (2006.01)
  *C23C 16/52* (2006.01)
  *G01B 11/06* (2006.01)
  *C23C 16/50* (2006.01)

(52) U.S. Cl.
  CPC .......... *C23C 16/52* (2013.01); *G01B 11/0625* (2013.01); *G01N 21/9081* (2013.01)

(58) Field of Classification Search
  USPC .................................. 356/445–448, 426–428
  See application file for complete search history.

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tompkins |
| 3,957,653 A | 5/1976 | Blecher |
| 4,111,326 A | 9/1978 | Percarpio |
| 4,118,972 A | 10/1978 | Goeppner |
| 4,134,832 A | 1/1979 | Heimreid |
| 4,136,794 A | 1/1979 | Percarpio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,810,752 A | 3/1989 | Bayan |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,978,714 A | 12/1990 | Bayan |
| 4,991,104 A | 2/1991 | Miller |
| 4,999,014 A | 3/1991 | Gold |
| 5,000,994 A | 3/1991 | Romberg |
| 5,009,646 A | 4/1991 | Sudo |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,288,560 A | 2/1994 | Sudo |
| 5,292,370 A | 3/1994 | Tsai |
| 5,294,011 A | 3/1994 | Konrad |
| 5,294,464 A | 3/1994 | Geisler |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |

(56) References Cited

U.S. PATENT DOCUMENTS

| | | | |
|---|---|---|---|
| 5,374,314 A | 12/1994 | Babacz |
| 5,378,510 A | 1/1995 | Thomas |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babcock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,550 A | 8/1998 | Phillips |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,093,175 A | 7/2000 | Gyure |

(56) References Cited

U.S. PATENT DOCUMENTS

| | | |
|---|---|---|
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,129,712 A | 10/2000 | Sudo |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negahdaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,344,034 B1 | 2/2002 | Sudo |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,282 B1 | 2/2003 | Sudo |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,010 B1 | 5/2003 | Gyure |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,645,635 B2 | 11/2003 | Muraki |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,663,603 B1 | 12/2003 | Gyure |
| 6,670,200 B2 | 12/2003 | Ushio |
| 6,673,199 B1 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |
| 6,749,078 B2 | 6/2004 | Iskra |
| 6,752,899 B1 | 6/2004 | Singh |
| 6,753,972 B1 | 6/2004 | Hirose |
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,822,015 B2 | 11/2004 | Muraki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |

(56) References Cited

U.S. PATENT DOCUMENTS

| | | |
|---|---|---|
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jaccoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,186,242 B2 | 3/2007 | Gyure |
| 7,188,734 B2 | 3/2007 | Konrad |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,214,214 B2 | 5/2007 | Sudo |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,547,297 B2 | 6/2009 | Brinkhues |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,582,868 B2 | 9/2009 | Jiang |
| 7,586,824 B2 | 9/2009 | Hirokane |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,682,816 B2 | 3/2010 | Kim |
| 7,691,308 B2 | 4/2010 | Brinkhues |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,202 B2 | 7/2010 | Miller |
| 7,749,914 B2 | 7/2010 | Honda |
| 7,754,302 B2 | 7/2010 | Yamasaki |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Soerensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |
| 7,922,958 B2 | 4/2011 | D'Arrigo |
| 7,927,315 B2 | 4/2011 | Sudo |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,002,754 B2 | 8/2011 | Kawamura |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,663 B2 | 11/2011 | Sudo |
| 8,066,854 B2 | 11/2011 | Storey |

(56) References Cited

U.S. PATENT DOCUMENTS

| | | |
|---|---|---|
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,101,674 B2 | 1/2012 | Kawauchi |
| 8,105,294 B2 | 1/2012 | Araki |
| 8,197,452 B2 | 6/2012 | Harding |
| 8,227,025 B2 | 7/2012 | Lewis |
| 8,258,486 B2 | 9/2012 | Avnery |
| 8,268,410 B2 | 9/2012 | Moelle |
| 8,273,222 B2 | 9/2012 | Wei |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130674 A1 | 9/2002 | Lagowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0102087 A1 | 6/2003 | Ito |
| 2003/0119193 A1 | 6/2003 | Hess |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kitzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |
| 2007/0148326 A1 | 6/2007 | Hastings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |

(56) References Cited

U.S. PATENT DOCUMENTS

| | | |
|---|---|---|
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0145271 A1 | 6/2008 | Kidambi |
| 2008/0187681 A1 | 8/2008 | Hofrichter |
| 2008/0195059 A1 | 8/2008 | Sudo |
| 2008/0202414 A1 | 8/2008 | Yan |
| 2008/0206477 A1 | 8/2008 | Rius |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0268252 A1 | 10/2008 | Garces |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | Mcelerea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Loboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Kang |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0042055 A1 | 2/2010 | Sudo |
| 2010/0075077 A1 | 3/2010 | Bicker |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0185157 A1 | 7/2010 | Kawamura |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0198554 A1 | 8/2010 | Skliar |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0264139 A1 | 10/2010 | Kawachi |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | Mcelerea |
| 2011/0046570 A1 | 2/2011 | Stout |
| 2011/0056912 A1 | 3/2011 | Matsuyama |
| 2011/0062047 A1 | 3/2011 | Haines |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan et al. |
| 2011/0220490 A1 | 9/2011 | Wei |
| 2011/0252899 A1 | 10/2011 | Felts |
| 2011/0253674 A1 | 10/2011 | Chung |
| 2011/0313363 A1 | 12/2011 | D'Souza et al. |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |

(56) References Cited

U.S. PATENT DOCUMENTS

| | | |
|---|---|---|
| 2012/0108058 A1 | 5/2012 | Ha |
| 2012/0109076 A1 | 5/2012 | Kawamura |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walther |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0305830 A1 | 10/2014 | Bicker |
| 2015/0165125 A1 | 6/2015 | Foucher |
| 2015/0224263 A1 | 8/2015 | Dugand |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CN | 2546041 Y | 4/2003 |
| CN | 1711310 A | 12/2005 |
| CN | 2766863 Y | 3/2006 |
| CN | 1898172 A | 1/2007 |
| CN | 201002786 Y | 1/2008 |
| CN | 101147813 A | 3/2008 |
| CN | 201056331 Y | 5/2008 |
| CN | 102581274 A | 7/2012 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0251812 A2 | 1/1988 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2602354 A1 | 6/2013 |
| EP | 2639330 A1 | 9/2013 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| JP | 56027330 A | 3/1981 |
| JP | 58154602 A | 9/1983 |
| JP | 59087307 A | 5/1984 |
| JP | 59154029 | 9/1984 |

(56) References Cited

FOREIGN PATENT DOCUMENTS

| | | |
|---|---|---|
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005-290560 | 10/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008-132766 A | 6/2008 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2012210315 A | 11/2012 |
| JP | 5362941 B2 | 12/2013 |
| KR | 10-2005-0100367 A | 10/2005 |
| KR | 10-2006-0029694 | 4/2006 |
| KR | 10-068559481 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO03033426 | 9/2002 |
| WO | WO02076709 A1 | 10/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | WO2005035147 A1 | 4/2005 |
| WO | WO2005/052555 A1 | 6/2005 |
| WO | WO2005051525 A1 | 6/2005 |
| WO | WO2005103605 A1 | 11/2005 |
| WO | WO2006012281 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |

(56) References Cited

FOREIGN PATENT DOCUMENTS

| | | |
|---|---|---|
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2013045671 A1 | 4/2013 |
| WO | WO2013/071138 | 5/2013 |
| WO | WO2013/071138 A1 | 5/2013 |
| WO | WO2013/170044 | 11/2013 |
| WO | WO2013/170052 | 11/2013 |
| WO | WO2014/008138 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |

OTHER PUBLICATIONS

Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
Patent Cooperation Treaty, International Preliminary Examining Authority, Notification of Transmittal of International Preliminary Report on Patentability, in international application No. PCT/US2011/036097, dated Nov. 13, 2012.
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).
European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).

PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
State Intellectual Property Office of the People's Republic of China, Notification of the Fourth Office Action in Application No. 201080029199.0, dated Mar. 18, 2015 (15 pages).
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, International application No. PCT/SU2013/071752, dated May 6, 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.

(56) References Cited

OTHER PUBLICATIONS

Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of Teh People's Republic of China, Notification of First Office Action in Application No. 201080029201.4, dated Mar. 37, 2013. (15 pages).
Japanese Patent Office, Notice of Reasons for Refusal, Patent Application No. 2013-510276, mailed Mar. 8, 2016 (15 pages).
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/ mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environment Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.

(56) References Cited

OTHER PUBLICATIONS

Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International Application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.
Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.108810022-3727/36123/003, IOP Electronic Journals, http://www.iop.org/EJ/abstract/0022-3727/36/23/003, printed Jul. 14, 2009.
Egitto, F.D., et al., Plasma Modification of Polymer Surfaces, Society of Vacuum Coaters, 36th Annual Technical Conference Proceedings, 1993, ISBN 1-878068-12-1, pp. 10-21.
Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/ abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

(56) References Cited

OTHER PUBLICATIONS

Felts, J.T., Transparent Gas Barrier Technologies, 33rd Annual Technical Conference Proceedings, 1990, ISBN 1-878068-09-1, pp. 184-193.

Finson, E., et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY.

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen für innovative Applikationen von Kunststoff-Substraten, HiCotec Smart Coating Solutions.

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

Lee, K. et al., The Ellipsometric Measurements of a Curved Surface, Japanese Journal of Applied Physics, vol. 44, No. 32, 2005, pp. L1015-L1018.

Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.

Masso, J.D., Evaluation of Scratch Resistant and Antireflective Coatings for Plastic Lenses, 32nd Annual Technical Conference Proceedings, 1989, p. 237-240.

Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.

Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.

Mount, E., Measuring Pinhole Resistance of Packaging, Corotec Corporation website, http://www.convertingmagazine.com, printed Jul. 13, 2009.

Murray, L. et al., The Impact of Foil Pinholes and Flex Cracks on the Moisture and Oxygen Barrier of Flexible Packaging.

Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.

Nelson, R.J., Scale-Up of Plasma Deposited SiOx Gas Diffusion Barrier Coatings, 35th Annual Technical Conference Proceedings, 1992, ISBN 1-878068-11-3, pp. 75-78.

Novotny, V. J., Ultrafast Ellipsometric Mapping of Thin Films, IBM Technical Disclosure Bulletin, vol. 37, No. 02A, Feb. 1994, pp. 187-188.

Rüger, M., Die Pulse Sind das Plus, PICVD-Beschichtungsverfahren.

Schultz, A. et al., Detection and Identification of Pinholes in Plasma-Polymerised Thin Film Barrier Coatings on Metal Foils, Surface & Coatings Technology 200, 2005, pp. 213-217.

Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.

Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.

Teyssedre, G. et al., Temperature Dependence of the Photoluminescence in Poly(Ethylene Terephthalate) Films, Polymer 42, 2001, pp. 8207-8216.

Tsung, L. et al., Development of Fast CCD Cameras for In-Situ Electron Microscopy, Microsc Microanal 14(Supp 2), 2008.

Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.

Yang, et al., Microstructure and tribological properties of SiOx/DLC films grown by PECVD, Surface and Coatings Technology, vol. 194, Issue 1, Apr. 20, 2005, pp. 128-135.

An 451, Accurate Thin Film Measurements by High-Resoluiton Transmission Electron Microscopy (HRTEM), Evans Alalytical Group, Version 1.0, Jun. 12, 2008, pp. 1-2.

Benefits of TriboGlide, TriboGlide Silicone-Free Lubrication Systems, http://www.triboglide.com/benfits.htm, printed Aug. 31, 2009.

Patent Cooperation Treaty, Written Opinion of the International Searching Authority with International Search Report in Application No. PCT/US2012/064489, dated Jan. 25, 2013.

Danish Patent and Trademark Office, Singapore Written Opinion, in Application No. 201108308-6, dated Dec. 6, 2012.

Danish Patent and Trademark Office, Singapore Search Report, in Application No. 201108308-6, dated Dec. 12, 2012.

Australian Government, IP Australia, Patent Examination Report No. 1, in Application No. 2012318242, dated Apr. 30, 2014. (6 pages).

State Intellectual Property Office of the People's Republic of China, Notification of the First Office Action, in Application No. 201180023461.5, dated May 21, 2014. (25 pages).

European Patent Office, Communication pursuant to Article 94(3) EPC, in Application No. 10162758.6 dated May 27, 2014. (7 pages).

European Patent Office, Communication pursuant to Article 94(3) EPC, in Application No. 10 162 758.6-1234, dated May 8, 2012 (6 pages).

PCT, Notification of Transmittal of the International Search Report and the Written Opinion of the International Searching Authority, or the Declaration, in International application No. PCT/US2013/040380, dated Sep. 3, 2013. (13 pages).

PCT, Notification of Transmittal of the International Search Report and the Written Opinion of the International Searching Authority, or the Declaration, in International application No. PCT/US2013/040368, dated Oct. 21, 2013. (21 pages).

PCT, Notification of Transmittal of the International Search Report and the Written Opinion of the International Searching Authority, or the Declaration, in International application No. PCT/US2013/048709, dated Oct. 2, 2013. (7 pages).

Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XP027113381, ISSN: 0257-8972 [retrieved on Jun. 16, 2010] abstract, p. 4014, right-hand column—p. 4015, figures 2, 3.

Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp.

(56) References Cited

OTHER PUBLICATIONS 2281-2286, XPO12004127, ISSN: 0734-2101, DOI: 10.1116/1.581341, p. 2283, right-hand column—p. 2284, left-hand column, figures 2, 4.

Coating Syringes, http://www.triboglide.com/syringes.htm, printed Aug. 31, 2009.

Coating/Production Process, http://www.triboglide.com/process.htm, printed Aug. 31, 2009.

Munich Exp, Materialica 2005: Fundierte Einblicke in den Werkstofsektor, Seite 1, von 4, ME095-6.

Schott Developing Syringe Production in United States, Apr. 14, 2009, http://www.schott.com/pharmaceutical_packaging, printed Aug. 31, 2009.

Sterile Prefillable Glass and Polymer Syringes, Schott forma vitrum, http://www.schott.com/pharmaceutical_packaging.

Transparent und recyclingfähig, neue verpackung, Dec. 2002, pp. 54-57.

European Patent Office, Communication with European Search Report, in Application No. 10162758.6, dated Aug. 19, 2010.

Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.

European Patent Office, Communication with extended Search Report, in Application No. EP 10162761.0, dated Feb. 10, 2011.

European Patent Office, Communication with partial Search Report, in Application No. EP 10162758.6, dated Aug. 19, 2010.

European Patent Office, Communication with extended Search Report, in Application No. EP 10162758.6, dated Dec. 21, 2010.

Yang, et al., Microstructure and tribological properties of SiOx/DLC films grown by PECVD, Surface and Coatings Technology, vol. 194 (2005), Apr. 20, 2005, pp. 128-135.

European Patent Office, Communication with extended European search report, in Application No. EP10162756.0, dated Nov. 17, 2010.

Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.

European Patent Office, Communication with extended European search report, in Application No. EP10162757.8, dated Nov. 10, 2010.

Patent Cooperation Treaty, Notification of Transmittal of the International Search Report and the Written Opinion of the International Searching Authority, in PCT/US2010/034568, dated Jan. 21, 2011.

Patent Cooperation Treaty, Notification of Transmittal of the International Search Report and the Written Opinion of the International Searching Authority, in PCT/US2010/034571, dated Jan. 26, 2011.

Patent Cooperation Treaty, Notification of Transmittal of the International Search Report and the Written Opinion of the International Searching Authority, in PCT/US2010/034576, dated Jan. 25, 2011.

Patent Cooperation Treaty, Notification of Transmittal of the International Search Report and the Written Opinion of the International Searching Authority, in PCT/US2010/034577, dated Jan. 21, 2011.

Patent Cooperation Treaty, Notification of Transmittal of the International Search Report and the Written Opinion of the International Searching Authority, in PCT/US2010/034582, dated Jan. 24, 2011.

European Patent Office, Communication with Extended Search Report, in Application No. EP 10162755.2, dated Nov. 9, 2010.

European Patent Office, Communication with Extended Search Report, in Application No. EP 10162760.2, dated Nov. 12, 2010.

PCT, Written Opinion of the International Searching Authority with International Search Report in Application No. PCT/US2010/034586, dated Mar. 15, 2011.

Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.

Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.

Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.

Mallikarjunan, Anupama et al, The Effect of Interfacial Chemistry on Metal Ion Penetration into Polymeric Films, Mat. Res. Soc. Symp. Proc. vol. 734, 2003, © Materials Research Society.

Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.

Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.

Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.

Australian Government, IP Australia, Patent Examination Report No. 1, in Application No. 2011252925, dated Sep. 6, 2013 (3 pages).

COATING INSPECTION METHOD

Priority is claimed to U.S. Provisional Appl. Ser. No. 61/721,092, filed Nov. 1, 2012.

U.S. Ser. No. 12/779,007, filed May 12, 2010, now U.S. Pat. No. 7,985,188, is hereby incorporated herein by reference in its entirety.

The present disclosure relates to the technical field of fabrication of coated vessels for storing biologically active compounds or blood. For example, the disclosure relates to a vessel processing system for coating of a vessel, vessel processing system for coating and inspection of a vessel, to a portable vessel holder for a vessel processing system, to a plasma enhanced chemical vapour deposition apparatus for coating an interior surface of a vessel, to a method for coating an interior surface of a vessel, to a method for coating an inspection of a vessel, to a method of processing a vessel, to the use of a vessel processing system, to a computer-readable medium and to a program element.

The present disclosure also relates to improved methods for processing vessels, for example multiple identical vessels used for venipuncture and other medical sample collection, pharmaceutical preparation storage and delivery, and other purposes. Such vessels are used in large numbers for these purposes, and must be relatively economical to manufacture and yet highly reliable in storage and use.

BACKGROUND OF THE DISCLOSURE

Evacuated blood collection tubes are used for drawing blood from a patient for medical analysis. The tubes are sold evacuated. The patient's blood is communicated to the interior of a tube by inserting one end of a double-ended hypodermic needle into the patient's blood vessel and impaling the closure of the evacuated blood collection tube on the other end of the double-ended needle. The vacuum in the evacuated blood collection tube draws the blood (or more precisely, the blood pressure of the patient pushes the blood) through the needle into the evacuated blood collection tube, increasing the pressure within the tube and thus decreasing the pressure difference causing the blood to flow. The blood flow typically continues until the tube is removed from the needle or the pressure difference is too small to support flow.

Evacuated blood collection tubes should have a substantial shelf life to facilitate efficient and convenient distribution and storage of the tubes prior to use. For example, a one-year shelf life is desirable, and progressively longer shelf lives, such as 18 months, 24 months, or 36 months, are also desired in some instances. The tube desirably remains essentially fully evacuated, at least to the degree necessary to draw enough blood for analysis (a common standard is that the tube retains at least 90% of the original draw volume), for the full shelf life, with very few (optimally no) defective tubes being provided.

A defective tube is likely to cause the phlebotomist using the tube to fail to draw sufficient blood. The phlebotomist might then need to obtain and use one or more additional tubes to obtain an adequate blood sample.

Prefilled syringes are commonly prepared and sold so the syringe does not need to be filled before use. The syringe can be prefilled with saline solution, a dye for injection, or a pharmaceutically active preparation, for some examples.

Commonly, the prefilled syringe is capped at the distal end, as with a cap, and is closed at the proximal end by its drawn plunger. The prefilled syringe can be wrapped in a sterile package before use. To use the prefilled syringe, the packaging and cap are removed, optionally a hypodermic needle or another delivery conduit is attached to the distal end of the barrel, the delivery conduit or syringe is moved to a use position (such as by inserting the hypodermic needle into a patient's blood vessel or into apparatus to be rinsed with the contents of the syringe), and the plunger is advanced in the barrel to inject the contents of the barrel.

One important consideration in manufacturing pre-filled syringes is that the contents of the syringe desirably will have a substantial shelf life, during which it is important to isolate the material filling the syringe from the barrel wall containing it, to avoid leaching material from the barrel into the prefilled contents or vice versa.

Since many of these vessels are inexpensive and used in large quantities, for certain applications it will be useful to reliably obtain the necessary shelf life without increasing the manufacturing cost to a prohibitive level. It is also desirable for certain applications to move away from glass vessels, which can break and are expensive to manufacture, in favor of plastic vessels which are rarely broken in normal use (and if broken do not form sharp shards from remnants of the vessel, like a glass tube would). Glass vessels have been favored because glass is more gas tight and inert to pre-filled contents than untreated plastics. Also, due to its traditional use, glass is well accepted, as it is known to be relatively innocuous when contacted with medical samples or pharmaceutical preparations and the like.

A further consideration when regarding syringes is to ensure that the plunger can move at a constant speed and with a constant force when it is pressed into the barrel. For this purpose, a lubricity layer, either on one or on both of the barrel and the plunger, is desirable.

U.S. Published Patent Application 20070229844 A1, Holz et al., incorporated here by reference in its entirety, discusses, "a method of measuring layer thicknesses and layer homogeneities in transparent, internally lubricant- and water-repulsion-coated containers, wherein a lens (2) focuses polychromatic light on to the internal coating (1B) of the container (1), the reflected light is detected again, coupled into a spectrometer and registered by way of a sensitive multichannel detector (7), and corresponding signals are transferred to an electronic evaluation means (8) which digitises the signals and computes the layer thickness from the interference pattern." Holz et al. discusses the use of this method to measure the thickness of baked on silicone oil coatings used as a lubricant or water repellent coating on syringes and other containers.

A non-exhaustive list of other patent documents of possible relevance includes U.S. Pat. Nos. 6,068,884 and 4,844,986 and U.S. Published Applications 20060046006 and 20040267194.

SUMMARY OF THE INVENTION

An aspect of the disclosure is a reflectometry method for detecting discontinuities in a CVD coating. The method can be carried out as follows.

An at least partially transparent thermoplastic vessel wall is provided. The vessel wall has an outside surface, an inside surface, and a CVD coating on at least one of the inside and outside surfaces. The vessel wall and the CVD coating have different indices of refraction.

Electromagnetic energy is impinged on multiple positions of the CVD coating under conditions effective to cause energy to reflect from the multiple positions of the CVD coating. The reflected energy is analyzed to determine whether the reflected energy includes at least one artifact of a discontinuity in the CVD coating.

The present method can be employed to measure any of the coatings described in this disclosure, for example, on any of the vessels described in this disclosure.

Figure 1:
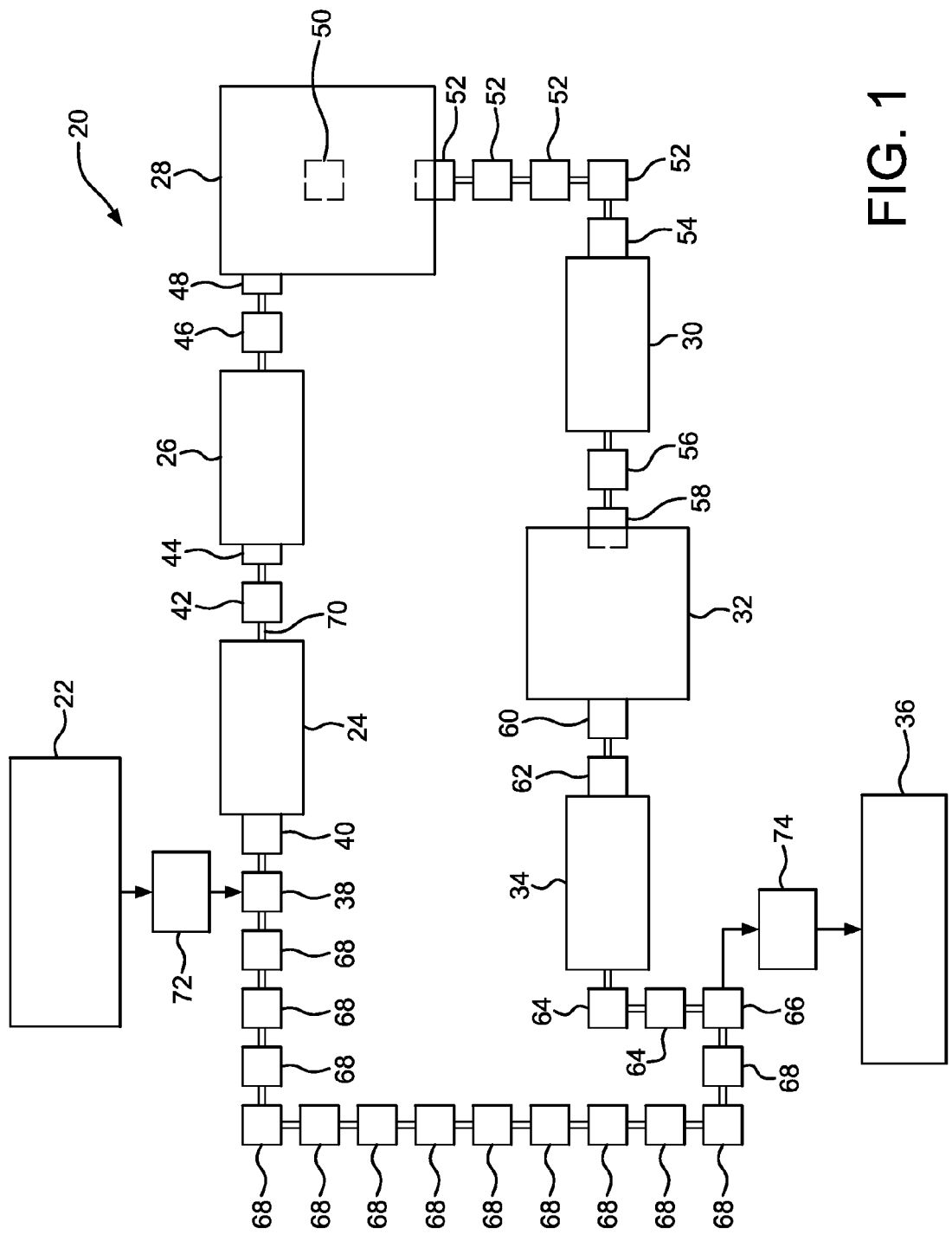
FIG. 1 is a schematic diagram showing a vessel processing system according to an embodiment of the disclosure.

The following reference characters are used in the drawing figures:

| 20 | Vessel processing system |
| 22 | Injection molding machine |
| 24 | Visual inspection station |
| 26 | Inspection station (pre-coating) |
| 28 | Coating station |
| 30 | Inspection station (post-coating) |
| 32 | Optical source transmission station (thickness) |
| 34 | Optical source transmission station (defects) |
| 36 | Output |
| 38 | Vessel holder |
| 40 | Vessel holder |
| 42 | Vessel holder |
| 44 | Vessel holder |
| 46 | Vessel holder |
| 48 | Vessel holder |
| 50 | Vessel holder |
| 52 | Vessel holder |
| 54 | Vessel holder |
| 56 | Vessel holder |
| 58 | Vessel holder |
| 60 | Vessel holder |
| 62 | Vessel holder |
| 64 | Vessel holder |
| 66 | Vessel holder |
| 68 | Vessel holder |
| 70 | Conveyor |
| 72 | Transfer mechanism (on) |
| 74 | Transfer mechanism (off) |
| 80 | Vessel |
| 82 | Opening |
| 84 | Closed end |
| 86 | Wall |
| 88 | Interior surface |
| 90 | Barrier layer |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 114 | Housing (of 50 or 112) |
| 116 | Collar |
| 118 | Exterior surface (of 80) |
| 132 | Light source |
| 134 | Side channel |
| 144 | PECVD gas source |
| 160 | Electrode |
| 162 | Power supply |
| 164 | Sidewall (of 160) |
| 166 | Sidewall (of 160) |
| 168 | Closed end (of 160) |
| 170 | Light source (FIG. 4) |
| 172 | Detector |
| 174 | Pixel (of 172) |
| 176 | Interior surface (of 172) |
| 182 | Aperture (of 186) |
| 184 | Wall (of 186) |
| 186 | Integrating sphere |
| 220 | Bearing surface (FIG. 2) |
| 222 | Bearing surface (FIG. 2) |
| 224 | Bearing surface (FIG. 2) |
| 226 | Bearing surface (FIG. 2) |
| 228 | Bearing surface (FIG. 2) |
| 230 | Bearing surface (FIG. 2) |
| 232 | Bearing surface (FIG. 2) |
| 234 | Bearing surface (FIG. 2) |
| 236 | Bearing surface (FIG. 2) |
| 238 | Bearing surface (FIG. 2) |
| 240 | Bearing surface (FIG. 2) |
| 250 | Syringe barrel |
| 252 | Syringe |
| 254 | Interior surface (of 250) |
| 256 | Back end (of 250) |
| 258 | Plunger (of 252) |
| 260 | Front end (of 250) |
| 262 | Cap |
| 264 | Interior surface (of 262) |
| 268 | Vessel |
| 270 | Closure |
| 272 | Interior facing surface |
| 274 | Lumen |

| | |
|---|---|
| 276 | Wall-contacting surface |
| 278 | Inner surface (of 280) |
| 280 | Vessel wall |
| 282 | Stopper |
| 284 | Shield |
| 286 | Lubricity layer |
| 288 | Barrier layer |
| 346 | Wall |
| 348 | Coating (on 346) |
| 350 | Permeation path |
| 354 | Gas molecule |
| 355 | Gas molecule |
| 356 | Interface (between 346 and 348) |
| 357 | Gas molecule |
| 358 | PET vessel |
| 359 | Gas molecule |
| 360 | Seal |
| 362 | Measurement cell |
| 364 | Vacuum pump |
| 366 | Arrows |
| 368 | Conical passage |
| 370 | Bore |
| 372 | Bore |
| 374 | Chamber |
| 376 | Chamber |
| 378 | Diaphragm |
| 380 | Diaphragm |
| 382 | Conductive surface |
| 384 | Conductive surface |
| 386 | Bypass |
| 390 | Plot (glass tube) |
| 392 | Plot (PET uncoated) |
| 394 | Main plot (SiO$_2$ coated) |
| 396 | Outliers (SiO$_2$ coated) |
| 544 | Syringe |
| 546 | Plunger |
| 548 | Body |
| 550 | Barrel |
| 552 | Interior surface (of 550) |
| 554 | Coating |
| 556 | Luer fitting |
| 558 | Luer taper |
| 560 | Internal passage (of 558) |
| 562 | Internal surface |
| 564 | Coupling |
| 566 | Male part (of 564) |
| 568 | Female part (of 564) |
| 570 | Barrier layer |
| 572 | Locking collar |
| 602 | Syringe exterior barrier layer |
| 604 | Lumen |
| 606 | Barrel exterior surface |
| 630 | Plots for uncoated COC |
| 632 | Plots for SiO$_x$ coated COC |
| 634 | Plots for glass |
| 710 | Vessel wall |
| 712 | Outside surface |
| 714 | Inside surface |
| 716 | CVD coating |
| 718 | Impinging electromagnetic energy |
| 720 | Source (of 18) |
| 722 | Reflected energy |
| 724 | Map (bar graph) |
| 726 | Map (shaded chart) |
| 728 | Image sensor (CCD) |
| 730 | Processor |
| 732 | Artifact |
| 734 | Partially silvered mirror |
| 736 | Lens |
| 738 | Focal point |
| 740 | Lens |
| 742 | Spectrometer |
| 744 | Multichannel detector |

DEFINITIONS

The following terms are used in this specification in the sense indicated here. A "discontinuity" is broadly defined as an area of a coating on a substrate that either is thinner than other areas, or that is absent altogether (i.e. an uncoated area). An example of a coating that is absent altogether would be a pinhole defect in the coating.

"At least partially transparent" as used here in reference to a material or object means that enough of the energy impinging on the object can be transmitted through the material or object to allow the reflected energy to be analyzed to determine the presence or absence of discontinuities in the coating.

The "color" of polychromatic energy is defined as its proportion of different wavelengths, which can be either visible or invisible to the human eye or a combination of both. For example, assume that (1) a first beam of polychromatic energy is composed of a 10 Watts per meter squared (W/m$^2$) component of 500 nm wavelength, a 3 W/m$^2$ component of 600 nm wavelength, and a 5 W/m$^2$ component of 700 nm wavelength; (2) a second beam of polychromatic energy is composed of a 10 W/m$^2$ component of 500 nm wavelength, a 10 W/m$^2$ component of 600 nm wavelength, and a 5 W/m$^2$ component of 700 nm wavelength; and (3) a third beam of polychromatic energy is composed of a 2 W/m$^2$ component of 500 nm wavelength, a 0.6 W/m$^2$ component of 600 nm wavelength, and a 1 W/m$^2$ component of 700 nm wavelength. The first beam and second beam are different colors as used herein because the second beam has relatively more 600 nm energy than the first, in relation to the intensities of the other wavelengths. The first and third beams are the same color. One is 20% as intense as the other, but both have the same proportions of 600 nm, 700 nm, and 800 nm component intensities.

A CVD coating analyzed as described in this specification can be prepared, for example, by plasma enhanced chemical vapor deposition treatment (PECVD), as described for example in U.S. Pat. No. 7,985,188, incorporated by reference above.

RF is radio frequency; sccm is standard cubic centimeters per minute.

The term "at least" in the context of the present disclosure means "equal or more" than the integer following the term. The word "comprising" does not exclude other elements or steps, and the indefinite article "a" or "an" does not exclude a plurality unless indicated otherwise.

"First" and "second" or similar references to, e.g., processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present disclosure, an "organosilicon precursor" is a compound having at least one of the linkage:

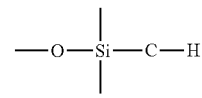

which is a tetravalent silicon atom connected to an oxygen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

In the context of the present disclosure, "essentially no oxygen" or (synonymously) "substantially no oxygen" is added to the gaseous reactant in some embodiments. This means that some residual atmospheric oxygen can be present in the reaction space, and residual oxygen fed in a previous step and not fully exhausted can be present in the reaction space, which are defined here as essentially no oxygen present. Essentially no oxygen is present in the gaseous reactant if the gaseous reactant comprises less than 1 vol % $O_2$, for example less than 0.5 vol % $O_2$, and optionally is $O_2$-free. If no oxygen is added to the gaseous reactant, or if no oxygen at all is present during PECVD, this is also within the scope of "essentially no oxygen."

A "vessel" in the context of the present disclosure can be any type of vessel with at least one opening and a wall defining an interior surface. The term "at least" in the context of the present disclosure means "equal or more" than the integer following the term. Thus, a vessel in the context of the present disclosure has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present disclosure, while the other openings are either capped or open. A vessel according to the present disclosure can be a sample tube, e.g. for collecting or storing biological fluids like blood or urine, a syringe (or a part thereof, for example a syringe barrel) for storing or delivering a biologically active compound or composition, e.g. a medicament or pharmaceutical composition, a vial for storing biological materials or biologically active compounds or compositions, a pipe, e.g. a catheter for transporting biological materials or biologically active compounds or compositions, or a cuvette for holding fluids, e.g. for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, e.g. in a sample tube or a syringe barrel. Sample tubes and syringes or their parts (for example syringe barrels) are contemplated.

A "hydrophobic layer" in the context of the present disclosure means that the coating lowers the wetting tension of a surface coated with the coating, compared to the corresponding uncoated surface. Hydrophobicity is thus a function of both the uncoated substrate and the coating. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity, and optionally can have a composition according to the empirical composition or sum formula $Si_wO_xC_yH_z$, for example where w is 1, x is from about 0.5 to about 2.4, y is from about 0.6 to about 3, and z is from about 2 to about 9, optionally where w is 1, x is from about 0.5 to 1, y is from about 2 to about 3, and z is from 6 to about 9. These values of w, x, y, and z are applicable to the empirical composition $Si_wO_xC_yH_z$ throughout this specification. The values of w, x, y, and z used throughout this specification should be understood as ratios or an empirical formula (e.g. for a coating), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

"Wetting tension" is a specific measure for the hydrophobicity or hydrophilicity of a surface. An optional wetting tension measurement method in the context of the present disclosure is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube.

Distinctions are made in this disclosure among "permeation," "leakage," and "surface diffusion" or "outgassing."

Figure 10:
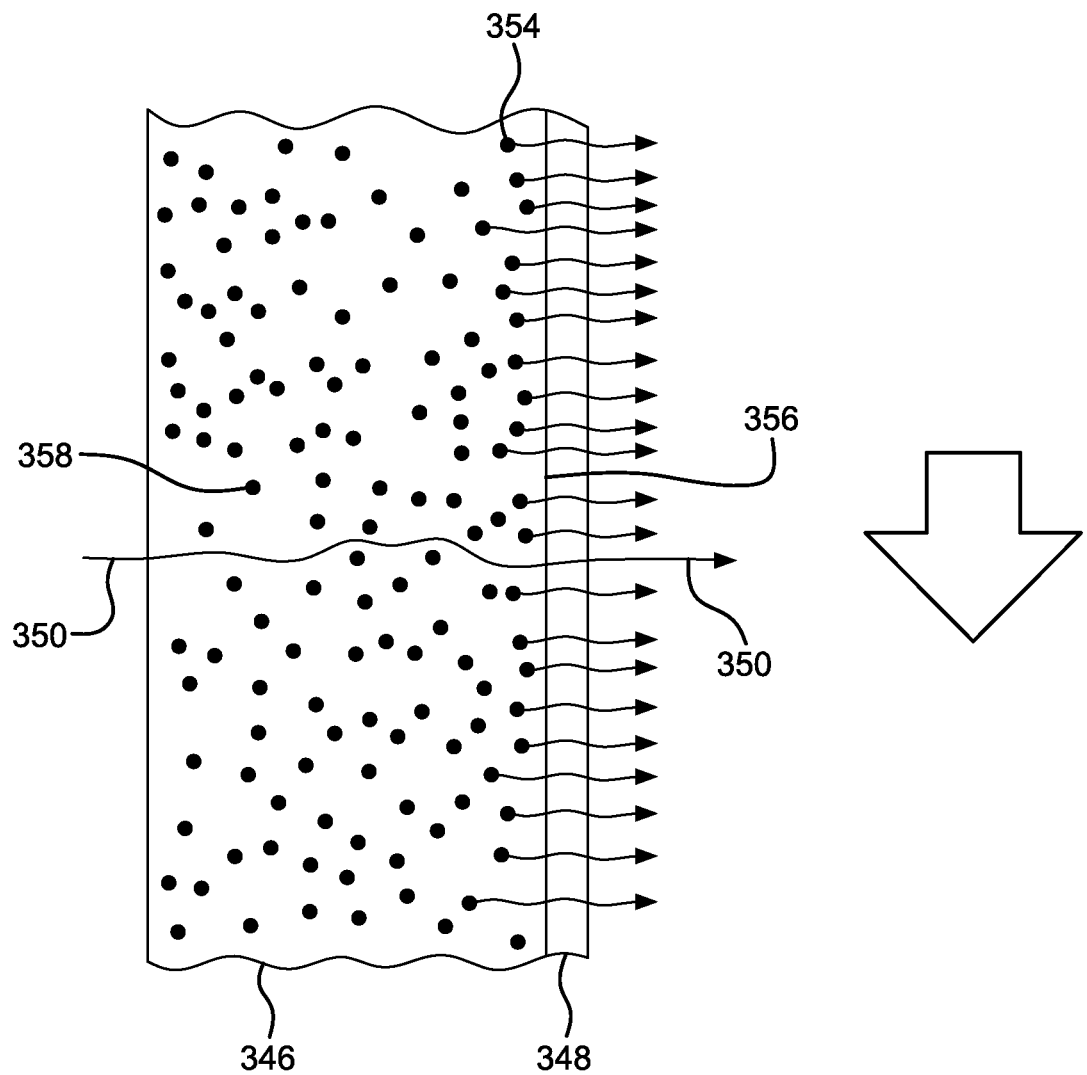
FIG. 10 is a schematic view showing outgassing of a material through a coating.

"Permeation" as used here in reference to a vessel is traverse of a material through a wall 346 or other obstruction, as from the outside of the vessel to the inside or vice versa along the path 350 in FIG. 10 or the reverse of that path.

"Outgassing" refers to the movement of an absorbed or adsorbed material such as the gas molecule 354 or 357 or 359 outward from within the wall 346 or coating 348 in FIG. 10, for example through the coating 348 (if present) and into the vessel 358 (to the right in FIG. 10). Outgassing can also refer to movement of a material such as 354 or 357 out of the wall 346, to the left as shown in FIG. 10, thus to the outside of the vessel 357 as illustrated. Outgassing can also refer to the removal of adsorbed material from the surface of an article, for example the gas molecule 355 from the exposed surface of the barrier coating 90.

"Leakage" refers to the movement of a material around the obstruction represented by the wall 346 and coating 348 rather than through or off the surface of the obstruction, as by passing between a closure and the wall of a vessel closed with a closure.

Permeation is indicative of the rate of gas movement through a material, devoid of gaps/defects and not relating to leaks or outgassing. Referring to FIG. 10, which shows a vessel wall or other substrate 346 having a barrier coating 348, permeation is traverse of a gas entirely through the substrate 346 and coating 348 along the path 350 through both layers. Permeation is regarded as a thermodynamic, thus relatively slow, process.

Permeation measurements are very slow, as the permeating gas must past entirely through an unbroken wall of the plastic article. In the case of evacuated blood collection tubes, a measurement of permeation of gas through its wall is conventionally used as a direct indication of the propensity of the vessel to lose vacuum over time, but commonly is an extremely slow measurement, commonly requiring a test duration of six days, thus not fast enough to support on-line coating inspection. Such testing is ordinarily used for off-line testing of a sample of vessels.

Permeation testing also is not a very sensitive measurement of the barrier efficacy of a thin coating on a thick substrate. Since all the gas flow is through both the coating and the substrate, variations in flow through the thick substrate will introduce variation that is not due to the barrier efficacy of the coating per se.

Surface diffusion and outgassing are synonyms. Each term refers to fluid initially adsorbed on or absorbed in a wall 346, such as the wall of a vessel, and caused to pass into the adjacent space by some motivating force, such as drawing a vacuum (creating air movement indicated by the arrow 352 of FIG. 10) within a vessel having a wall to force fluid out of the wall into the interior of the vessel. Outgassing or diffusion is regarded as a kinetic, relatively quick process. It is contemplated that, for a wall 346 having substantial resistance to permeation along the path 350, outgassing will quickly dislodge the molecules such as 354 that are closest to the interface 356 between the wall 346 and the barrier layer 348. This differential outgassing is suggested by the large number of molecules such as 354 near the interface 356 shown as outgassing, and by the large number of other molecules such as 358 that are further from the interface 356 and are not shown as outgassing.

DETAILED DESCRIPTION OF THE PREFERRED EMBODIMENTS

The present disclosure will now be described more fully with reference to the accompanying drawings, in which several embodiments are shown. This disclosure can, however, be embodied in many different forms and should not be construed as limited to the embodiments set forth here. Rather, these embodiments are examples of the disclosure, which has the full scope indicated by the language of the claims. Like numbers refer to like or corresponding elements throughout.

Figure 2:
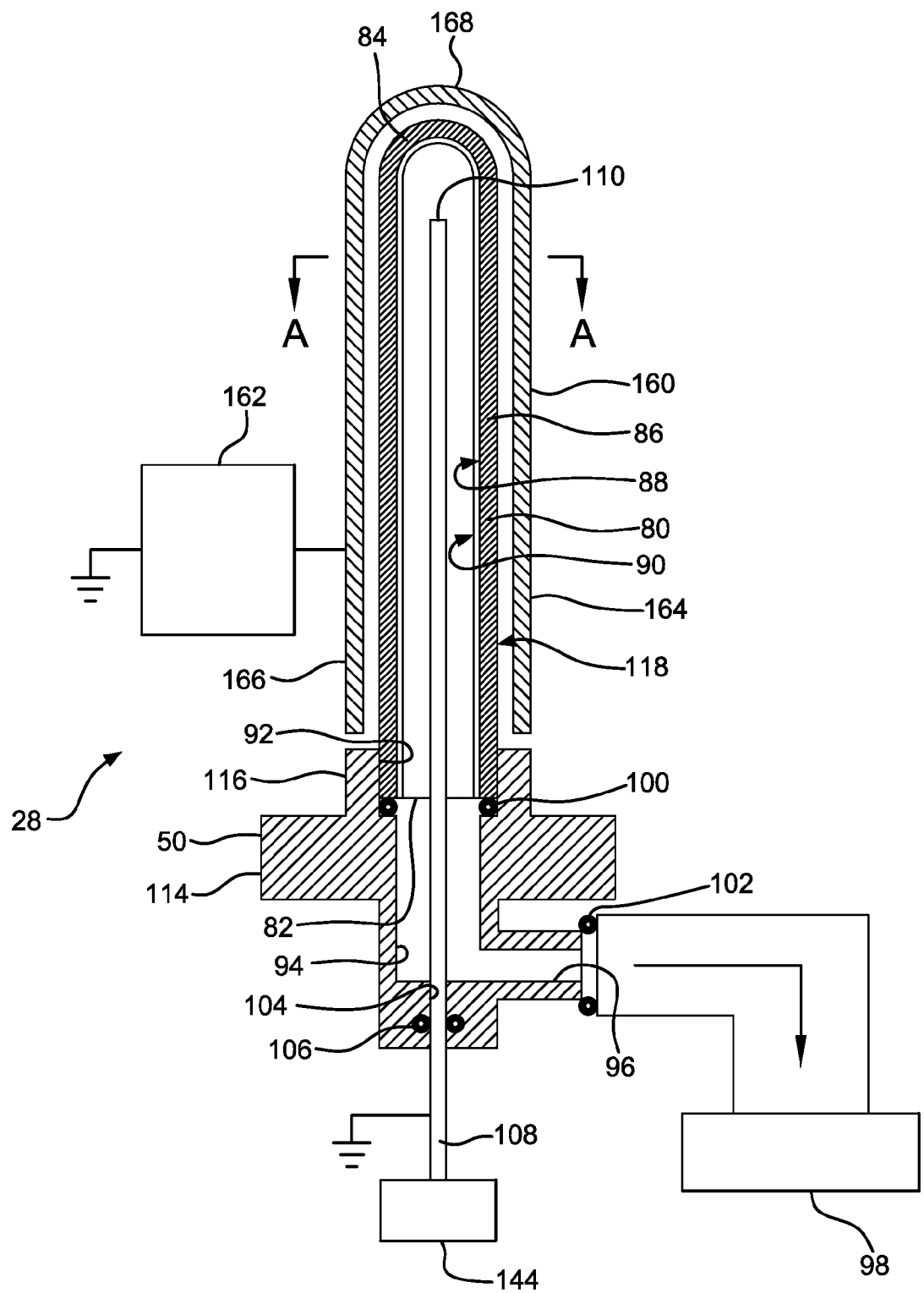
FIG. 2 is a schematic sectional view of a vessel holder in a coating station according to an embodiment of the disclosure.
Figure 4:
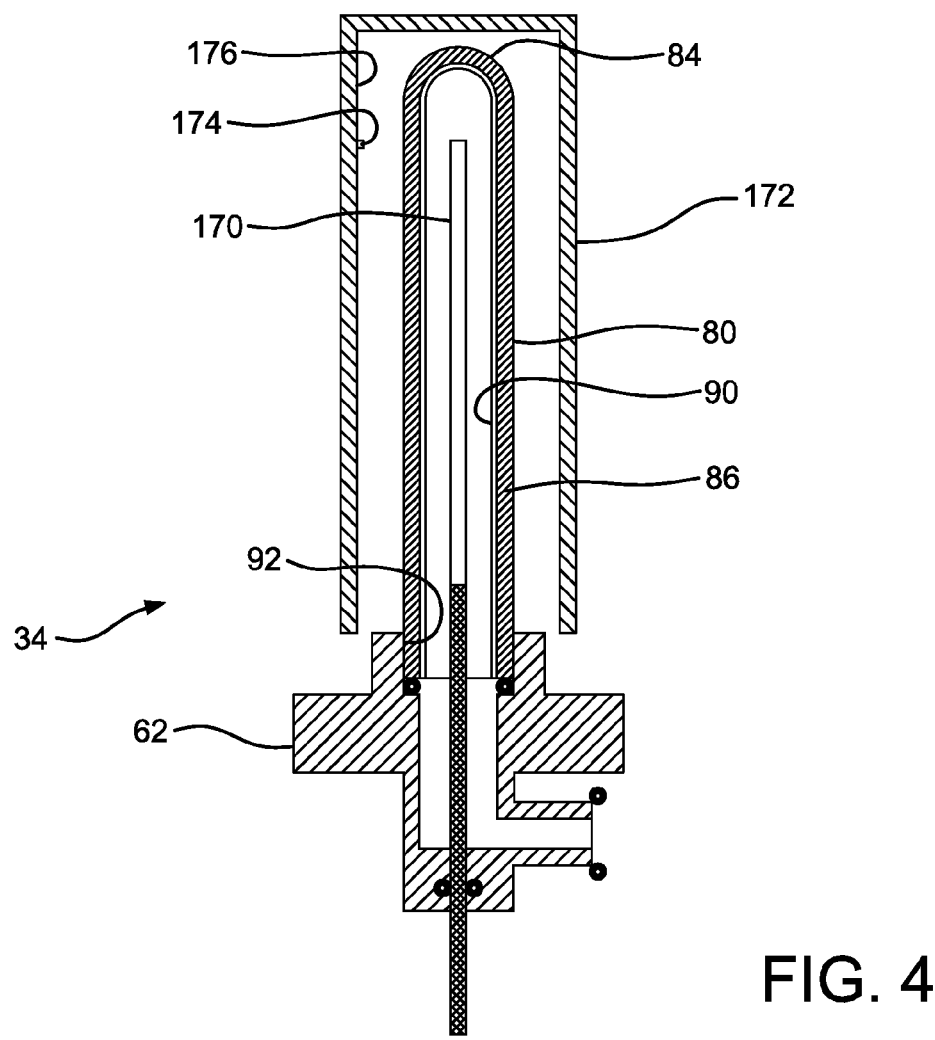
FIG. 4 is a schematic sectional view of a light source and detector for vessel inspection apparatus, with a vessel in place.

FIGS. 1, 2, and 4 show a method for processing a vessel 80 to provide a coating or layer. The method can be carried out as follows.

A vessel 80 can be provided having an opening 82 and a wall 86 defining an interior surface 88. As one embodiment, the vessel 80 can be formed in and then removed from a mold. Quickly moving the vessel 80 from the mold 22 to the vessel port 92 reduces the dust or other impurities that can reach the surface 88 and occlude or prevent adhesion of the barrier or other type of coating 90. Also, the sooner a vacuum is drawn on the vessel 80 after it is made, the less chance any particulate impurities have of adhering to the interior surface 88.

The substrate or vessel wall can comprise glass or a polymer, for example a polycarbonate polymer, an olefin polymer, a cyclic olefin copolymer, a polypropylene polymer, a polyester polymer, a polyethylene terephthalate polymer or a combination of any two or more of these.

A vessel holder such as 50 comprising a vessel port 92 can be provided. The opening 82 of the vessel 80 can be seated on the vessel port 92. Before, during, or after seating the opening 82 of the vessel 80 on the vessel port 92, the vessel holder such as 40 (for example in FIG. 3) can be transported into engagement with one or more of the bearing surfaces 220-240 to position the vessel holder 40 with respect to the processing device or station such as 24.

Figure 3:
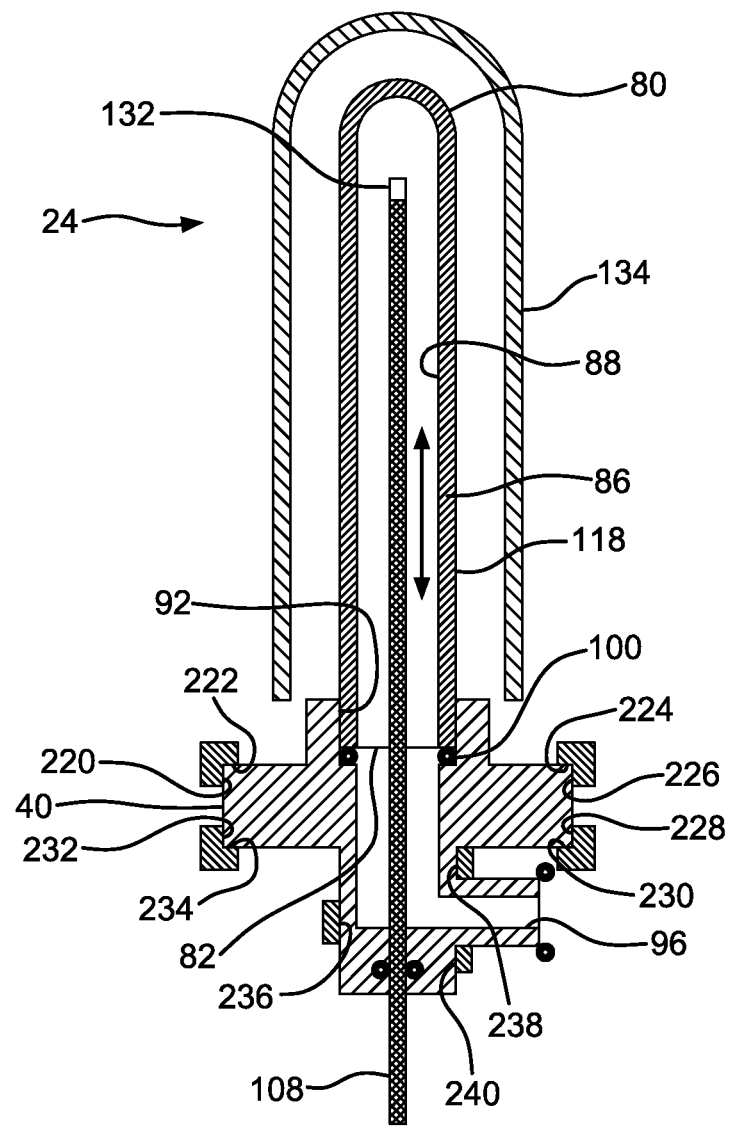
FIG. 3 is a view similar to FIG. 2 of vessel inspection apparatus.

One, more than one, or all of the processing stations such as 24-34, as illustrated by the station 24 shown in FIG. 3, can include a bearing surface, such as one or more of the bearing surfaces 220, 222, 224, 226, 228, 230, 232, 234, 236, 238, or 240, for supporting one or more vessel holders such as 40 in a predetermined position while processing the interior surface 88 of the seated vessel 80 at the processing station or device such as 24. These bearing surfaces can be part of stationary or moving structure, for example tracks or guides that guide and position the vessel holder such as 40 while the vessel is being processed. For example, the downward-facing bearing surfaces 222 and 224 locate the vessel holder 40 and act as a reaction surface to prevent the vessel holder 40 from moving upward when the probe 108 is being inserted into the vessel holder 40. The reaction surface 236 locates the vessel holder and prevents the vessel holder 40 from moving to the left while a vacuum source 98 (per FIG. 2) is seated on the vacuum port 96. The bearing surfaces 220, 226, 228, 232, 238, and 240 similarly locate the vessel holder 40 and prevent horizontal movement during processing. The bearing surfaces 230 and 234 similarly locate the vessel holder such as 40 and prevent it from moving vertically out of position. Thus, a first bearing surface, a second bearing surface, a third bearing surface, or more can be provided at each of the processing stations such as 24-34.

The interior surface 88 of the seated vessel 80 can be processed via the vessel port 92 at the first processing station, which can be, as one example, the barrier application or other type of coating station 28 shown in FIG. 2. In the apparatus of FIG. 1, the vessel coating station 28 can be, for example, a PECVD apparatus as further described below, operated under suitable conditions to deposit a SiOx barrier or other type of coating 90 on the interior surface 88 of a vessel 80, as shown in FIG. 2.

Referring especially to FIGS. 1 and 2, the processing station 28 can include an electrode 160 fed by a radio frequency power supply 162 for providing an electric field for generating plasma within the vessel 80 during processing. In this embodiment, the probe 108 is also electrically conductive and is grounded, thus providing a counter-electrode within the vessel 80. Alternatively, in any embodiment the outer electrode 160 can be grounded and the probe 108 directly connected to the power supply 162.

In the embodiment of FIG. 2, the outer electrode 160 can either be generally cylindrical or a generally U-shaped elongated channel as illustrated in FIG. 2. Each illustrated embodiment has one or more sidewalls, such as 164 and 166, and optionally a top end 168, disposed about the vessel 80 in close proximity.

The first processing device such as the probe 108 can be moved into operative engagement with the vessel holder 50, or vice versa. The interior surface 88 of the seated vessel 80 is processed via the vessel port 92 using the first processing device or probe 108.

The barrier layer can be a full or partial coating of any of the presently described barrier layers.

The thickness of this and other coatings can be measured, for example, by transmission electron microscopy (TEM).

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered layer of platinum (50-100 nm thick) using a K575X Emitech coating system, or the samples can be coated directly with the protective sputtered Pt layer. The coated samples can be placed in an FEI FIB200 FIB system. An additional layer of platinum can be FIB-deposited by injection of an oregano-metallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using a proprietary in-situ FIB lift-out technique. The cross sections can be attached to a 200 mesh copper TEM grid using FIB-deposited platinum.

One or two windows in each section, measuring 8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec.(×4) |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

The vessel holder 50 and seated vessel 80 can be transported from the first processing station 28 to a second processing station, for example the processing station 32. The interior surface 88 of the seated vessel 80 can be processed via the vessel port 92 at the second processing station such as 32.

One suitable processing station such as 32 is provided to employ reflectometry to measure the integrity of the barrier coating. Referring to FIGS. 18-21, apparatus and methods for vessel inspection are shown, employing reflectometry analysis as disclosed for example in US 2007/0229844 A1. This analysis can be carried out in any of the inspection stations. The apparatus includes a vessel, in this case a thermoplastic syringe barrel defining a generally cylindrical vessel wall 710. Note that a thermoplastic syringe barrel is not disclosed in US 2007/0229844 A1. The vessel wall 710 can be any part of any of the vessels defined in this description. The thermoplastic vessel wall 710 has an outside surface 712, an inside surface 714, and a CVD coating 716 on at least one of the inside and outside surfaces 712, 714. The CVD coating can be any of the lubricity, barrier, or hydrophobic coatings defined in this description. The vessel wall 710 and the CVD coating 716 optionally have different indices of refraction. This is useful so energy can be reflected from an interface between the vessel wall 710 and the CVD coating 716.

Electromagnetic energy 718 generated from an energy source 720, which can be a laser or a non-coherent energy source, can be impinged on the CVD coating 716. Various arrangements can be used.

Figure 18:
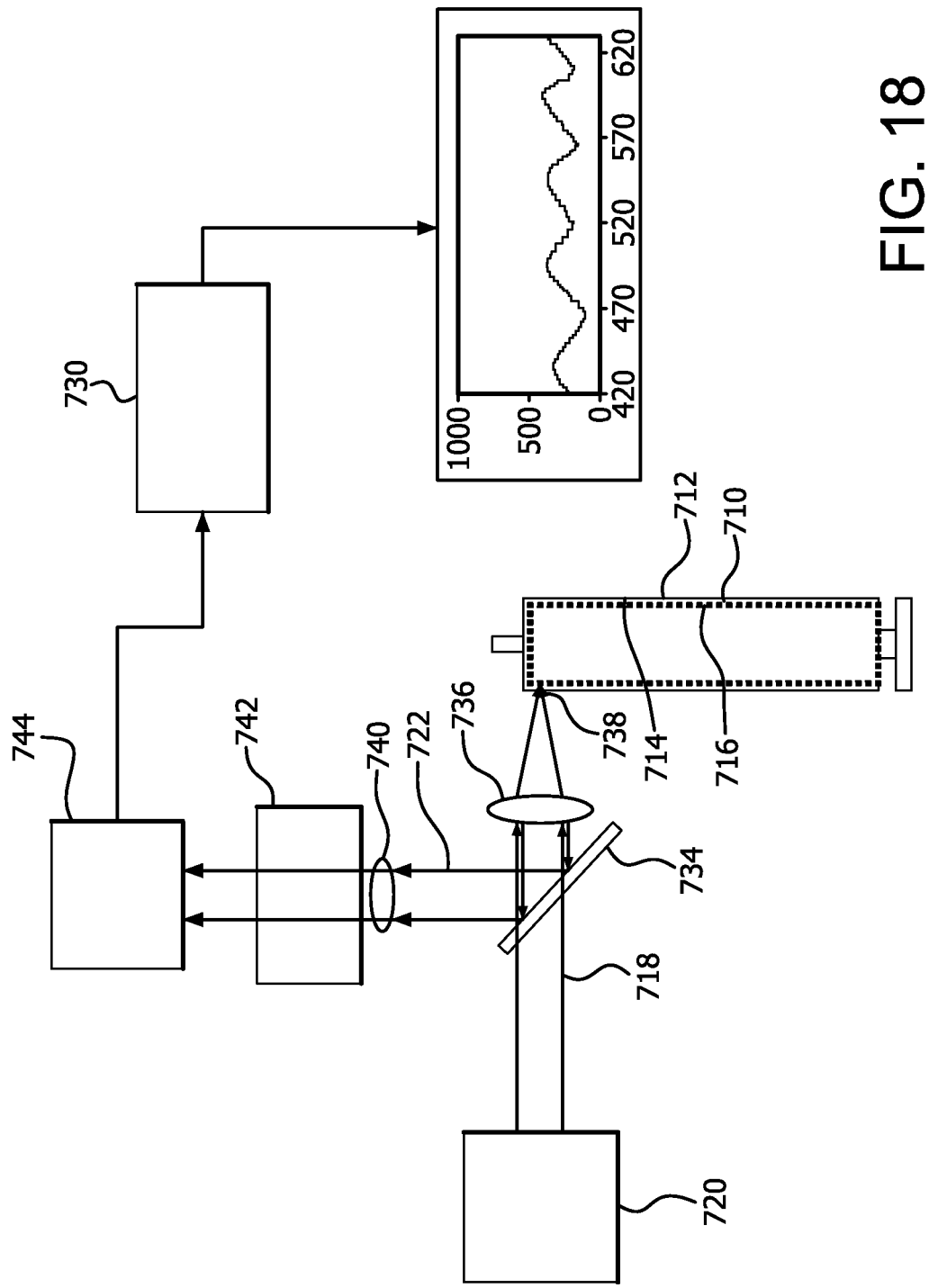
FIG. 18 is a schematic view of an embodiment of apparatus useful for carrying out the present disclosure.

In the embodiment of FIG. 18, the impinging energy 718 is polychromatic and passes through a partially silvered mirror 734 which transmits a portion of the energy 718, as illustrated, and also reflects a portion of the energy 718 toward the bottom of the figure. The reflected energy is not used in the illustrated apparatus, although detection apparatus for analyzing the color, intensity, or other features of the impinging energy 718 optionally can be provided in line with the beam of reflected energy.

The energy 718 is focused by a lens 736 to be concentrated at a focal point 738. The energy 722 is reflected from the CVD coating. The reflected energy 722 normally will be a different color from the impinging energy 718, as certain wavelengths are reinforced and others are canceled to form an interference pattern due to reflection of the impinging energy 718 from different points, such as the near and far surfaces of the coating 716.

The reflected energy 722 follows a reverse path through the lens 736, is partially reflected upward by the partially silvered mirror 734 (and in this case the transmitted portion is not used), and is directed to apparatus generally including a lens 740, a spectrometer 742, and a multichannel detector 744 for providing data indicative of the intensity of different detected wavelengths of the reflected energy 722. The data is input to the processor 730, which is programmed to determine the color of the reflected energy 722, and from that the thickness of the coating 718 at the point of measurement.

Figure 19:
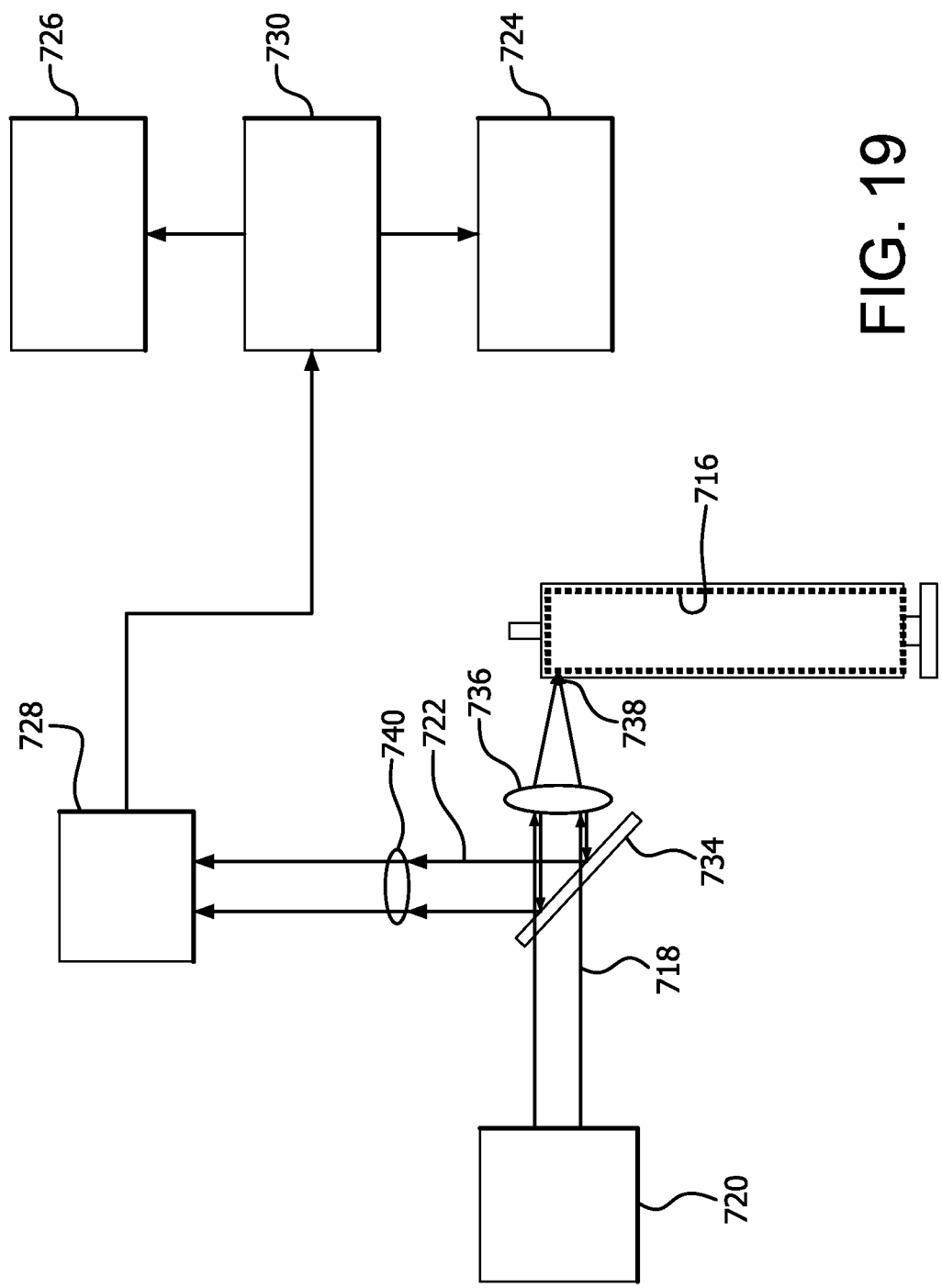
FIG. 19 is a schematic view of another embodiment of apparatus useful for carrying out the present disclosure.

The embodiment of FIG. 19 is a different arrangement for making an imagewise record or map of the reflected light 722 from different portions of the coating 716, showing at least one artifact 732 of a discontinuity in the CVD coating 716 (if such a discontinuity is present and detectable). Two illustrations of such maps are 724 and 726.

The map 724 is a one-dimensional map showing the thickness of the coating 716 along a line scanned by relative movement between the focal point 738 and the vessel wall 710, which can either be due to rotation or axial movement of the vessel 710 or focal point 738 relative to each other. To inspect multiple scan lines or the entire vessel, multiple such scans can be made. If the scanned line is axial, the remainder of the vessel is scanned by progressively rotating the vessel wall 710 between each scan to scan a circumferentially displaced line. Alternatively the scanned line can be circumferential and the vessel can progressively be moved axially to scan additional lines needed to cover the entire vessel.

The map 726 is a two-dimensional map, showing by color or shading differences the thickness of the coating 716 over an area, which optionally can be a cylindrical section of the vessel wall 710 or a greater or lesser area of the entire vessel. For example, a dark artifact 732 is shown. In the event of a pinhole or other break in the coating 716, it is contemplated that little or no light will be reflected back from the coating, leaving as an artifact on the map 726 a dark spot where little or no light is reflected back, corresponding to the position of the pinhole. Since this artifact represents a region of very low intensity of all wavelengths, it optionally can be detected without resolving the reflected energy 722 by wavelength.

The present reflectometry method for detecting discontinuities in a chemical vapor deposition CVD coating can be carried out as follows.

A thermoplastic vessel wall 710 can be provided having an outside surface 712, an inside surface 714, and a CVD coating 716 on at least one of the inside and outside surfaces 712, 714. The vessel wall 710 and the CVD coating 716 have different indices of refraction, which is a precondition for providing reflected light from both interfaces with the coating 716—the interface between the wall 710 and the coating 716, and the interface between the coating 716 and the space within the vessel wall 710. It is contemplated that reflections from these respective interfaces occur due to this difference in indices of refraction. The respective reflections from these two interfaces produce an interference pattern in the reflected energy 722, which allows a calculation of the thickness of the coating 718.

The method is carried out by impinging electromagnetic energy 718 from an energy source 720 on multiple positions of the CVD coating 716 under conditions effective to cause energy 722 to reflect from the multiple positions of the CVD coating 716. The reflected energy 722 is analyzed to determine whether the reflected energy 722 includes at least one artifact 732 of a discontinuity in the CVD coating 716.

In one optional variation of any embodiment of the method, the energy source 720 provides energy 718 within at least a portion of the wavelength range from 40 to 1100 nm.

Another optional variation of any embodiment of the method includes mapping the reflected energy 722 to the multiple positions of the CVD coating 716, producing a map 724 or 726.

Another optional variation of any embodiment of the method includes recording the map 724 or 726 of the reflected energy 722.

Another optional variation of any embodiment of the method includes recording the map 724 or 726 by a charge-coupled device image sensor 728 configured for converting the recorded map 724 or 726 to a data stream.

In another optional variation of any embodiment of the method, the analyzing step is carried out by a processor 730 programmed for analyzing the data stream to find at least one artifact 732 representing a discrete area of the image of contrasting brightness relative to the background of the discrete area, representing a discontinuity.

Another optional variation of any embodiment of the method includes determining the area of the discontinuity.

Another optional variation of any embodiment of the method includes configuring the processor 730 to determine the aggregate area of all discontinuities detected in the CVD coating 716.

In another optional variation of any embodiment of the method the impinging energy 718 is polychromatic.

In another optional variation of any embodiment of the method the reflected energy 722 contains interference patterns resulting from its interaction with the CVD coating 716.

In another optional variation of any embodiment of the method the color of the reflected energy 722 differs from the color of the impinging energy 718.

In another optional variation of any embodiment of the method the vessel wall 710 is at least partially transparent.

In another optional variation of any embodiment of the method the vessel wall 710 is positioned such that the impinging energy 718 passes through the vessel wall 710 to reach the CVD coating 716. This is desirable because the method optionally can be carried out without inserting any structure within any part of the vessel.

In another optional variation of any embodiment of the method the vessel wall 710 is positioned such that the reflected energy 722 passes through the vessel wall 710 before the reflected energy 722 is analyzed. This is desirable because the method optionally can be carried out without inserting any structure within any part of the vessel.

In another optional variation of any embodiment of the method the vessel wall 710 is positioned such that the impinging energy 718 impinges inwardly on the outside of the vessel wall 710 and reflects from a CVD coating 716 positioned on the inside of the vessel wall 710. Again, this is desirable because the method optionally can be carried out without inserting any structure within any part of the vessel, even for a coating disposed on the inside surface of the vessel wall.

Many variations of the basic structure described above and shown in FIGS. 18-21 are contemplated, including the following variations which are usable separately or together in practicing the present technology.

A rule of thumb is that the X-ray, gamma ray, or electron beam energy source 720 desirably can have a suitable wavelength of the infrared, visible light, ultraviolet light, X-ray, gamma ray, or electron beam energy on the same order of magnitude as the thickness of the coating to be measured. Measurement of very thin coatings, such as those having a thickness of 5 to 1000 nm, optionally 10 to 500 nm, optionally 10 to 500 nm, optionally 10 to 200 nm, optionally 20 to 200 nm, optionally 20 to 100 nm, is contemplated.

The discontinuity detector 730 can be a computer processor programmed for analyzing the data stream to find at least one artifact representing a discrete area of the image of contrasting brightness relative to the background of the discrete area.

One option is that the discontinuity detector 730 can be configured to determine the area of an artifact. Another option is that the discontinuity detector 730 can be configured to determine the aggregate area of one or more artifacts. Determining the areas of artifacts may be important if the CVD coating 720 is intended to be a gas barrier coating, such as the $SiO_x$ coatings described in this specification, and the inspection method is being used to determine the continuity of the coating. If the artifact is a break in the coating, such as a pinhole, the area of the artifact(s) can be used to provide an indication of the gas leakage rate of the discontinuity.

Commercial equipment analogous to that shown in FIGS. 18 and 19, contemplated for practicing the present disclosure, is available from RAP.ID Particle Systems GmbH, Berlin, Germany. Such equipment can be modified by a person skilled in the art to specifically look for discontinuities, instead of or additional to mapping the coating thickness.

Still another processing device such as a light source 170 (FIG. 4) can be provided for further processing vessels such as 80. A vessel 80 is provided having an opening 82 and a wall 86 defining an interior surface 88. A vessel holder 50 is provided comprising a vessel port 92. The opening 82 of the vessel 80 is seated on the vessel port 92.

The other processing device such as 170 (FIG. 4) is then moved into operative engagement with the vessel holder 50, or vice versa. The interior surface 88 of the seated vessel 80 is processed via the vessel port 92 using the other processing device such as the light source 170.

Optionally, any number of additional processing steps can be provided. For example, a yet another processing device 34 can be provided for processing vessels 80. The processing device 34 can be moved into operative engagement with the vessel holder 50, or vice versa. The interior surface of the seated vessel 80 can be processed via the vessel port 92 using the processing device 34.

VI. Vessel Inspection

A vessel processing method is contemplated for any of the inspection stations in which the interior surface of the vessel is inspected for defects before and/or after applying the barrier coating or other coatings.

In an embodiment, the station or device 26 (which can also function as the station or device 28 for applying a coating) can be used as follows for barometric vessel inspection of the vessel as molded. With either or both of the valves 136 and 148 open, the vessel 80 can be evacuated to a desired degree, optionally to a very low pressure such as less than 10 Torr, optionally less than 1 Torr. Whichever of the valves 136 and 148 is initially open can then be closed, isolating the evacuated interior 154 of the vessel 80 and the pressure gauge 152 from ambient conditions and from the vacuum source 98. The change in pressure over a measurement time, whether due to the ingress of gas through the vessel wall or outgassing from the material of the wall and/or a coating on the vessel wall, can then be sensed and used to calculate the rate of ingress of ambient gas into the vessel 80 as mounted on the vessel holder 44. For the present purpose, outgassing is defined as the release of adsorbed or occluded gases or water vapor from the vessel wall, optionally in at least a partial vacuum.

Another optional modification can be to provide the ambient gas at a higher pressure than atmospheric pressure. This again can increase the rate of gas transfer through a barrier or other type of layer, providing a measurable difference in a shorter time than if a lower ambient pressure were provided. Or, gas can be introduced into the vessel 80 at a higher than atmospheric pressure, again increasing the transfer rate through the wall 86.

Optionally, the vessel inspection at the station or by the device 26 can be modified by providing an inspection gas, such as helium, on an upstream side with respect to the substrate, either within or outside the vessel 80, and detecting it on the downstream side. A low-molecular-weight gas, such as hydrogen, or a less expensive or more available gas, such as oxygen or nitrogen, can also be used as an inspection gas.

Helium is contemplated as an inspection gas that can increase the rate of leak or permeation detection, as it will pass through an imperfect barrier or other type of coating, or past a leaking seal, much more quickly than the usual ambient gases such as nitrogen and oxygen in ordinary air. Helium has a high transfer rate through many solid substrates or small gaps because it: (1) is inert, so it is not adsorbed by the substrate to any great degree, (2) is not ionized easily, so its molecules are very compact due to the high level of attraction between its electrons and nucleus, and (3) has a molecular weight of 4, as opposed to nitrogen (molecular weight 28) and oxygen (molecular weight 32), again making the molecules more compact and easily passed through a porous substrate or gap. Due to these factors, helium will travel through a barrier having a given permeability much more quickly than many other gases. Also, the atmosphere contains an extremely small proportion of helium naturally, so the presence of additional helium can be relatively easy to detect, particularly if the helium is introduced within the vessel 80 and detected outside the vessel 80 to measure leakage and permeation. The helium can be detected by a pressure drop upstream of the substrate or by other means, such as spectroscopic analysis of the downstream gas that has passed through the substrate.

An example of barometric vessel inspection by determining the oxygen concentration from $O_2$ fluorescence detection follows.

An Excitation Source (Ocean Optics USB-LS-450 Pulsed Blue LED), fiber assembly (Ocean Optics QBIF6000-VIS-NIR), a spectrometer (USB4000-FL Fluorescence Spectrometer), an oxygen sensor probe (Ocean Optics FOXY-R), and a vacuum feed through adaptor (like VFT-1000-VIS-275) connected to a vacuum source are used. A vacuum can be applied to remove the ambient air, and when the vessel is at a defined pressure any oxygen content that has leaked or permeated in to refill the vessel from the ambient air can be determined using the detection system. A coated tube replaces the uncoated tube and $O_2$ concentration measurement can be taken. The coated tube will demonstrate reproducibly different atmospheric oxygen content than the uncoated sample due to differential $O_2$ surface absorption on the coated tube (an $SiO_x$ surface, versus the uncoated PET or glass surface) and/or a change in $O_2$ diffusion rate from the surface. Detection time can be less than one second.

These barometric methods should not be considered limited to a specific gas sensed (helium detection or other gases can be considered) or a specific apparatus or arrangement.

Another station or device shown in FIG. 1 is a post-coating processing station or device 30, which can be configured to inspect the interior surface of a vessel 80 for defects, as by measuring the air pressure loss or mass flow rate or volume flow rate through a vessel wall or outgassing of a vessel wall to be sure the vessel has been coated. The post-coating device 30 can operate similarly to the pre-coating inspection device 26, except that better performance (less leakage or permeation at given process conditions) optionally can be required to pass the inspection provided by the device 30, since in the illustrated embodiment a barrier or other type of coating has been applied by the station or device 28 before the station or device 30 is reached. Less leakage or permeation at the station or device 30 indicates that the barrier coating is functioning at least to a degree.

An outgassing test can be carried out by the device 30, for example. An outgassing test is described in U.S. Pat. No. 7,985,188, incorporated by reference above, as well as by FIGS. 10-13 and 17 and the accompanying text of the present disclosure. The outgassing test is specifically contemplated for use with a reflectometry test as described in this specification to measure the respective characteristics of particular vessels being processed.

In the case of a coated wall, the inventors have found that diffusion/outgassing can be used to determine the coating integrity. Optionally, a pressure differential can be provided across the barrier layer by at least partially evacuating the lumen or interior space of the vessel. This can be done, for example, by connecting the lumen via a duct to a vacuum source to at least partially evacuate the lumen. For example, referring to FIG. 10, an uncoated PET wall 346 of a vessel that has been exposed to ambient air will outgas from its interior surface a certain number of oxygen and other gas molecules such as 354 for some time after a vacuum is drawn. If the same PET wall is coated on the interior with a barrier coating 348, the barrier coating will stop, slow down, or reduce this outgassing. This is true for example of an $SiO_x$ barrier coating 348, which outgasses less than a plastic surface. By measuring this differential of outgassing between coated and uncoated PET walls, the barrier effect of the coating 348 for the outgassed material can be rapidly determined.

If the barrier coating 348 is imperfect, due to known or theoretical holes, cracks, gaps or areas of insufficient thickness or density or composition, the PET wall will outgas preferentially through the imperfections, thus increasing the total amount of outgassing. The primary source of the collected gas is from the dissolved gas or vaporizable constituents in the (sub)surface of the plastic article next to the coating, not from outside the article. The amount of outgassing beyond a basic level (for example the amount passed or released by a standard coating with no imperfections, or the least attainable degree of imperfection, or an average and acceptable degree of imperfection) can be measured in various ways to determine the integrity of the coating.

The measurement can be carried out, for example, by providing an outgassing measurement cell communicating between the lumen and the vacuum source.

The measurement cell can implement any of a variety of different measurement technologies. One example of a suitable measurement technology is micro-flow technology. For example, the mass flow rate of outgassed material can be measured. The measurement can be carried out in a molecular flow mode of operation. An exemplary measurement is a determination of the volume of gas outgassed through the barrier layer per interval of time.

The outgassed gas on the lower-pressure side of the barrier layer can be measured under conditions effective to distinguish the presence or absence of the barrier layer. Optionally, the conditions effective to distinguish the presence or absence of the barrier layer include a test duration of less than one minute, or less than 50 seconds, or less than 40 seconds, or less than 30 seconds, or less than 20 seconds, or less than 15 seconds, or less than 10 seconds, or less than 8 seconds, or less than 6 seconds, or less than 4 seconds, or less than 3 seconds, or less than 2 seconds, or less than 1 second.

Optionally, the measurement of the presence or absence of the barrier layer can be confirmed to at least a six-sigma level of certainty within any of the time intervals identified above.

Optionally, the outgassed gas on the lower-pressure side of the barrier layer is measured under conditions effective to determine the barrier improvement factor (BIF) of the barrier layer, compared to the same material without a barrier layer. A BIF can be determined, for example, by providing two groups of identical containers, adding a barrier layer to one group of containers, testing a barrier property (such as the rate of outgassing in micrograms per minute or another suitable measure) on containers having a barrier, doing the same test on containers lacking a barrier, and taking a ratio of the properties of the materials with versus without a barrier. For example, if the rate of outgassing through the barrier is one-third the rate of outgassing without a barrier, the barrier has a BIF of 3.

Optionally, outgassing of a plurality of different gases can be measured, in instances where more than one type of gas is present, such as both nitrogen and oxygen in the case of outgassed air. Optionally, outgassing of substantially all or all of the outgassed gases can be measured. Optionally, outgassing of substantially all of the outgassed gases can be measured simultaneously, as by using a physical measurement like the combined mass flow rate of all gases.

Measuring the number or partial pressure of individual gas species (such as oxygen or helium) outgassed from the sample can be done more quickly than barometric testing, but the rate of testing is reduced to the extent that only a fraction of the outgassing is of the measured species. For example, if nitrogen and oxygen are outgassed from the PET wall in the approximately 4:1 proportion of the atmosphere, but only oxygen outgassing is measured, the test would need to be run five times as long as an equally sensitive test (in terms of number of molecules detected to obtain results of sufficient statistical quality) that measures all the species outgassed from the vessel wall.

For a given level of sensitivity, it is contemplated that a method that accounts for the volume of all species outgassed from the surface will provide the desired level of confidence more quickly than a test that measures outgassing of a specific species, such as oxygen atoms. Consequently, outgassing data having practical utility for in-line measurements can be generated. Such in-line measurements can optionally be carried out on every vessel manufactured, thus reducing the number of idiosyncratic or isolated defects and potentially eliminating them (at least at the time of measurement).

In a practical measurement, a factor changing the apparent amount of outgassing is leakage past an imperfect seal, such as the seal of the vessel seated on a vacuum receptacle as the vacuum is drawn in the outgassing test. Leakage means a fluid bypassing a solid wall of the article, for example fluid passing between a blood tube and its closure, between a syringe plunger and syringe barrel, between a container and its cap, or between a vessel mouth and a seal upon which the vessel mouth is seated (due to an imperfect or mis-seated seal). The word "leakage" is usually indicative of the movement of gas/gas through an opening in the plastic article.

Leakage and (if necessary in a given situation) permeation can be factored into the basic level of outgassing, so an acceptable test result assures both that the vessel is adequately seated on the vacuum receptacle (thus its seated surfaces are intact and properly formed and positioned), the vessel wall does not support an unacceptable level of permeation (thus the vessel wall is intact and properly formed), and the coating has sufficient barrier integrity.

Outgassing can be measured in various ways, as by barometric measurement (measuring the pressure change within the vessel in a given amount of time after the initial vacuum is drawn) or by measuring the partial pressure or flow rate of gas outgassed from the sample. Equipment is available that measures a mass flow rate in a molecular flow mode of operation. An example of commercially available equipment of this type employing Micro-Flow Technology is available from ATC, Inc., Indianapolis, Ind. See U.S. Pat. Nos. 5,861,546, 6,308,556, 6,584,828 and EP1356260, which are incorporated by reference here, for a further description of this known equipment. See also Example 3 in this specification, showing an example of outgassing measurement to distinguish barrier coated polyethylene terephthalate (PET) tubes from uncoated tubes very rapidly and reliably.

Figure 12:
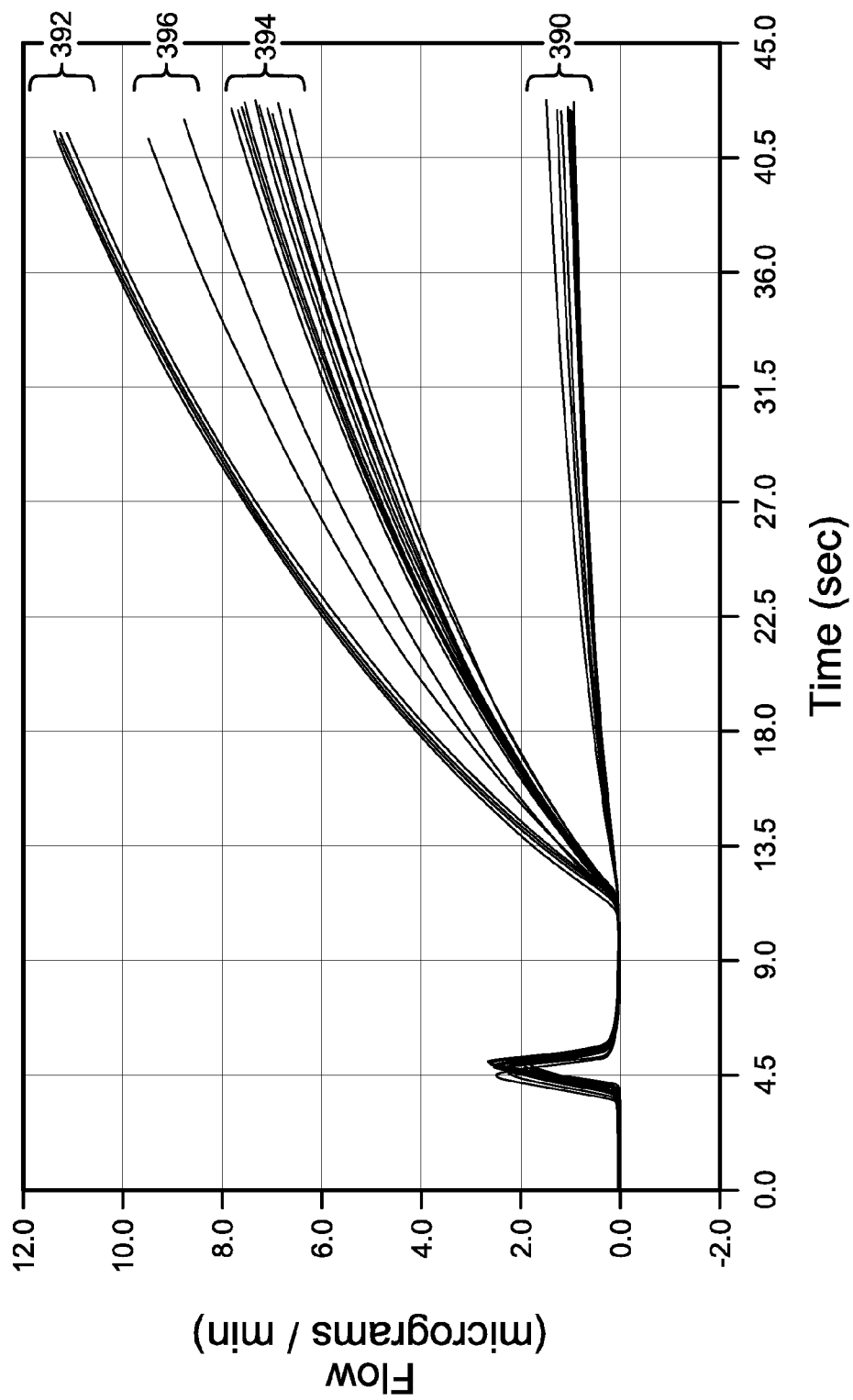
FIG. 12 is a plot of outgassing mass flow rate measured on the test-set-up of FIG. 11 for multiple vessels.

For a vessel made of polyethylene terephthalate (PET), the microflow rate is much different for the $SiO_x$ coated surface versus an uncoated surface. For example, in Working Example 3 in this specification, the microflow rate for PET was 8 or more micrograms after the test had run for 30 seconds, as shown in FIG. 12. This rate for uncoated PET was much higher than the measured rate for $SiO_x$-coated PET, which was less than 6 micrograms after the test had run for 30 sec, again as shown in FIG. 12.

One possible explanation for this difference in flow rate is that uncoated PET contains roughly 0.7 percent equilibrium moisture; this high moisture content is believed to cause the observed high microflow rate. With an $SiO_x$-coated PET plastic, the $SiO_x$ coating can have a higher level of surface moisture than an uncoated PET surface. Under the testing conditions, however, the barrier coating is believed to prevent additional desorption of moisture from the bulk PET plastic, resulting in a lower microflow rate. The microflow rates of oxygen or nitrogen from the uncoated PET plastic versus the $SiO_x$ coated PET would also be expected to be distinguishable.

Modifications of the above test for a PET tube might be appropriate when using other materials. For example, polyolefin plastics tend to have little moisture content. An example of a polyolefin having low moisture content is TOPAS® cyclic olefin copolymer (COC), having an equilibrium moisture content (0.01 percent) and moisture permeation rate much lower than for PET. In the case of COC, uncoated COC plastic can have microflow rate similar to, or even less than, $SiO_x$-coated COC plastic. This is most likely due to the higher surface moisture content of the $SiO_x$-coating and the lower equilibrium bulk moisture content and lower permeation rate of an uncoated COC plastic surface. This makes differentiation of uncoated and coated COC articles more difficult.

The present disclosure shows that exposure of the to-be-tested surfaces of COC articles to moisture (uncoated and coated) results in improved and consistent microflow separation between uncoated and $SiO_x$-coated COC plastics. This is shown in Example 9 in this specification and FIG. 17. The moisture exposure can be simply exposure to relative humidity ranging from 35%-100%, either in a controlled relative humidity room or direct exposure to a warm (humidifier) or cold (vaporizer) moisture source, with the latter preferred.

While the validity and scope of the disclosure are not limited according to the accuracy of this theory, it appears the moisture doping or spiking of the uncoated COC plastic increases its moisture or other outgassable content relative to the already saturated $SiO_x$-coated COC surface. This can also be accomplished by exposing the coated and uncoated tubes to other gases including oxygen, nitrogen, or their mixtures, for example air.

Thus, before measuring the outgassed gas, the barrier layer can be contacted with water, for example water vapor. Water vapor can be provided, for example, by contacting the barrier layer with air at a relative humidity of 35% to 100%, alternatively 40% to 100%, alternatively 40% to 50%. Instead of or in addition to water, the barrier layer can be contacted with oxygen, nitrogen or a mixture of oxygen and nitrogen, for example ambient air. The contacting time can be from 10 seconds to one hour, alternatively from one minute to thirty minutes, alternatively from 5 minutes to 25 minutes, alternatively from 10 minutes to 20 minutes.

Figure 5:
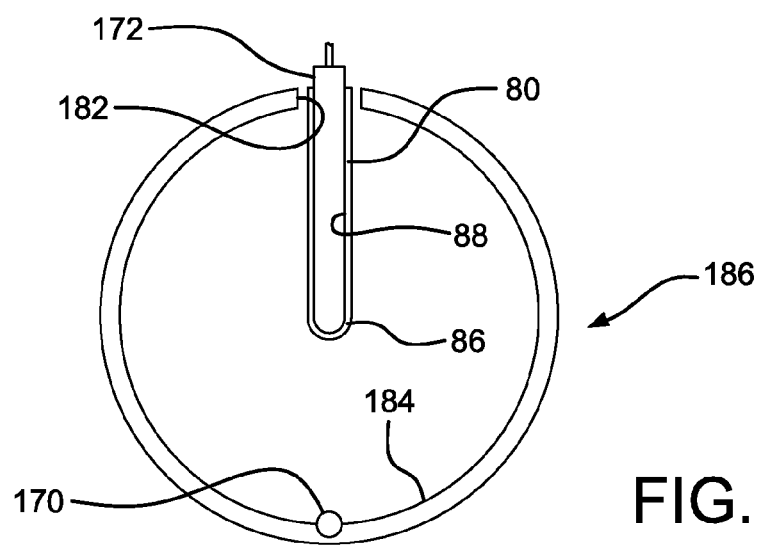
FIG. 5 is a detail view similar to FIG. 4 of a light source and detector that are reversed compared to the corresponding parts of FIG. 3.

Alternatively, the wall 346 which will be outgassing can be spiked or supplemented from the side opposite a barrier layer 348, for example by exposing the left side of the wall 346 as shown in FIG. 5 to a material that will ingas into the wall 346, then outgas either to the left or to the right as shown in FIG. 10. Spiking a wall or other material such as 346 from the left by ingassing, then measuring outgassing of the spiked material from the right (or vice versa) is distinguished from permeation measurement because the material spiked is within the wall 346 at the time outgassing is measured, as opposed to material that travels the full path 350 through the wall at the time gas presented through the coating is being measured. The ingassing can take place over a long period of time, as one embodiment before the coating 348 is applied, and as another embodiment after the coating 348 is applied and before it is tested for outgassing.

Another potential method to increase separation of microflow response between uncoated and $SiO_x$-coated plastics is to modify the measurement pressure and/or temperature. Increasing the pressure or decreasing the temperature when measuring outgassing can result in greater relative binding of water molecules in $SiO_x$-coated COC than in uncoated COC. Thus, the outgassed gas can be measured at a pressure from 0.1 Torr to 100 Torr, alternatively from 0.2 Torr to 50 Torr, alternatively from 0.5 Torr to 40 Torr, alternatively from 1 Torr to 30 Torr, alternatively from 5 Torr to 100 Torr, alternatively from 10 Torr to 80 Torr, alternatively from 15 Torr to 50 Torr. The outgassed gas can be measured at a temperature from 0° C. to 50° C., alternatively from 0° C. to 21° C., alternatively from 5° C. to 20° C.

Another way contemplated for measuring outgassing, in any embodiment of the present disclosure, is to employ a microcantilever measurement technique. Such a technique is contemplated to allow measurement of smaller mass differences in outgassing, potentially on the order of $10^{-12}$ g. (picograms) to $10^{-15}$ g. (femtograms). This smaller mass detection permits differentiation of coated versus uncoated surfaces as well as different coatings in less than a second, optionally less than 0.1 sec., optionally a matter of microseconds.

Microcantilever (MCL) sensors in some instances can respond to the presence of an outgassed or otherwise provided material by bending or otherwise moving or changing shape due to the absorption of molecules. Microcantilever (MCL) sensors in some instances can respond by shifting in resonance frequency. In other instances, the MCL sensors can change in both these ways or in other ways. They can be operated in different environments such as gaseous environment, liquids, or vacuum. In gas, microcantilever sensors can be operated as an artificial nose, whereby the bending pattern of a microfabricated array of eight polymer-coated silicon cantilevers is characteristic of the different vapors from solvents, flavors, and beverages. The use of any other type of electronic nose, operated by any technology, is also contemplated.

Several MCL electronic designs, including piezoresistive, piezoelectric, and capacitive approaches, have been applied and are contemplated to measure the movement, change of shape, or frequency change of the MCLs upon exposure to chemicals.

One specific example of measuring outgassing can be carried out as follows. At least one microcantilever is provided that has the property, when in the presence of an outgassed material, of moving or changing to a different shape. The microcantilever is exposed to the outgassed material under conditions effective to cause the microcantilever to move or change to a different shape. The movement or different shape is then detected.

As one example, the movement or different shape can be detected by reflecting an energetic incident beam from a portion of the microcantilever that moves or changes shape, before and after exposing the microcantilever to outgassing, and measuring the resulting deflection of the reflected beam at a point spaced from the cantilever. The shape is optionally measured at a point spaced from the cantilever because the amount of deflection of the beam under given conditions is proportional to the distance of the point of measurement from the point of reflection of the beam.

Several suitable examples of an energetic incident beam are a beam of photons, a beam of electrons, or a combination of two or more of these. Alternatively, two or more different beams can be reflected from the MCL along different incident and/or reflected paths, to determine movement or shape change from more than one perspective. One specifically contemplated type of energetic incident beam is a beam of coherent photons, such as a laser beam. "Photons" as discussed in this specification are inclusively defined to include wave energy as well as particle or photon energy per se.

An alternative example of measurement takes advantage of the property of certain MCLs of changing in resonant frequency when encountering an environmental material in an effective amount to accomplish a change in resonant frequency. This type of measurement can be carried out as follows. At least one microcantilever is provided that resonates at a different frequency when in the presence of an outgassed material. The microcantilever can be exposed to the outgassed material under conditions effective to cause the microcantilever to resonate at a different frequency. The different resonant frequency is then detected by any suitable means.

As one example, the different resonant frequency can be detected by inputting energy to the microcantilever to induce it to resonate before and after exposing the microcantilever to outgassing. The differences between the resonant frequencies of the MCL before and after exposure to outgassing are determined. Alternatively, instead of determining the difference in resonant frequency, an MCL can be provided that is known to have a certain resonant frequency when in the presence of a sufficient concentration or quantity of an outgassed material. The different resonant frequency or the resonant frequency signaling the presence of a sufficient quantity of the outgassed material is detected using a harmonic vibration sensor.

As one example of using MCL technology for measuring outgassing, an MCL device can be incorporated into a quartz vacuum tube linked to a vessel and vacuum pump. A harmonic vibration sensor using a commercially available piezoresistive cantilever, Wheatstone bridge circuits, a positive feedback controller, an exciting piezoactuator and a phase-locked loop (PLL) demodulator can be constructed. See, e.g., Hayato Sone, Yoshinori Fujinuma and Sumio Hosaka Picogram Mass Sensor Using Resonance Frequency Shift of Cantilever, Jpn. J. Appl. Phys. 43 (2004) 3648;

Hayato Sone, Ayumi Ikeuchi, Takashi Izumi, Haruki Okano and Sumio Hosaka Femtogram Mass Biosensor Using Self-Sensing Cantilever for Allergy Check, Jpn. J. Appl. Phys. 43 (2006) 2301).

To prepare the MCL for detection, one side of the microcantilever can be coated with gelatin. See, e.g., Hans Peter Lang, Christoph Gerber, STM and AFM Studies on (Bio) molecular Systems: Unravelling the Nanoworld, Topics in Current Chemistry, Volume 285/2008. Water vapor desorbing from the evacuated coated vessel surface binds with the gelatin, causing the cantilever to bend and its resonant frequency to change, as measured by laser deflection from a surface of the cantilever. The change in mass of an uncoated vs. coated vessel is contemplated to be resolvable in fractions of seconds and be highly reproducible. The articles cited above in connection with cantilever technology are incorporated here by reference for their disclosures of specific MCLs and equipment arrangements that can be used for detecting and quantifying outgassed species.

Alternative coatings for moisture detection (phosphoric acid) or oxygen detection can be applied to MCLs in place of or in addition to the gelatin coating described above.

It is further contemplated that any of the presently contemplated outgassing test set-ups can be combined with an $SiO_x$ coating station. In such an arrangement, the measurement cell 362 could be as illustrated above, using the main vacuum channel for PECVD as the bypass 386. In an embodiment, the measurement cell generally indicated as 362 of FIG. 11 can be incorporated in a vessel holder such as 50 in which the bypass channel 386 is configured as the main vacuum duct 94 and the measurement cell 362 is a side channel.

This combination of the measurement cell 362 with the vessel holder 50 would optionally allow the outgassing measurement to be conducted without breaking the vacuum used for PECVD. Optionally, the vacuum pump for PECVD would be operated for a short, optionally standardized amount of time to pump out some or all of the residual reactant gases remaining after the coating step (a pumpdown of less than one Torr, with a further option of admitting a small amount of air, nitrogen, oxygen, or other gas to flush out or dilute the process gases before pumping down). This would expedite the combined processes of coating the vessel and testing the coating for presence and barrier level.

Many other applications for the presently described outgassing measurements and all the other described barrier measurement techniques will be evident to the skilled person after reviewing this specification.

The identity of a vessel 80 measured at two different stations or by two different devices can be ascertained by placing individual identifying characteristics, such as a bar code, other marks, or a radio frequency identification (RFID) device or marker, on each of the vessel holders 38-68 and matching up the identity of vessels measured at two or more different points about the endless conveyor shown in FIG. 1. Since the vessel holders can be reused, they can be registered in a computer database or other data storage structure as they reach the position of the vessel holder 40 in FIG. 1, just after a new vessel 80 has been seated on the vessel holder 40, and removed from the data register at or near the end of the process, for example as or after they reach the position of the vessel holder 66 in FIG. 1 and the processed vessel 80 is removed by the transfer mechanism 74.

A processing station or device 32 can be provided and configured to further inspect a vessel, for example a barrier or other type of coating applied to the vessel, for defects. One embodiment, the station or device 32 determines the optical source transmission of the coating, as a measurement of the thickness of the coating. The barrier or other type of coating, if suitably applied, can make the vessel 80 more transparent, even though additional material has been applied, as it provides a more uniform surface.

Other measures of the thickness of the coating are also contemplated, as by using interference measurements to determine the difference in travel distance between an energy wave that bounces off the inside of the coating 90 (interfacing with the atmosphere within the vessel interior 154) and an energy wave that bounces off the interior surface 88 of the vessel 80 (interfacing with the outside of the coating 90). As is well known, the difference in travel distance can be determined directly, as by measuring the time of arrival of the respective waves with high precision, or indirectly, as by determining what wavelengths of the incident energy are reinforced or canceled, in relation to the test conditions.

Another measurement technique that can be carried out to check coating integrity is an ellipsometric measurement on the device. In this case, a polarized laser beam can be projected either from the inside or the outside of the vessel 80. In the case of a laser beam projected from the inside, the laser beam can be pointed orthogonally at the surface and then either the transmitted or reflected beam can be measured. The change in beam polarity can be measured. Since a coating or treatment on the surface of the device will impact (change) the polarization of the laser beam, changes in the polarity can be the desired result. The changes in the polarity are a direct result of the existence of a coating or treatment on the surface and the amount of change is related to the amount of treatment or coating.

If the polarized beam is projected from the outside of the device, a detector can be positioned on the inside to measure the transmitted component of the beam (and the polarity determined as above). Or, a detector can be placed outside of the device in a position that can correspond to the reflection point of the beam from the interface between the treatment/coating (on the inside of the device). The polarity change(s) can then be determined as detailed above.

In addition to measuring optical properties and/or leak rates as described above, other probes and/or devices can be inserted into the inside of the device and measurements made with a detector apparatus. This apparatus is not limited by the measurement technique or method. Other test methods that employ mechanical, electrical, or magnetic properties, or any other physical, optical, or chemical property, can be utilized.

During the plasma treatment setup, an optical detection system optionally can be used to record the plasma emission spectrum (wavelength and intensity profile), which corresponds to the unique chemical signature of the plasma environment. This characteristic emission spectrum provides confirmation that the coating has been applied and treated. The system also offers a real-time precision measurement and data archive tool for each part processed.

Any of the above methods can include as a step inspecting the interior surface 88 of a vessel 80 for defects at a processing station such as 24, 26, 30, 32, or 34. Inspecting can be carried out, as at the stations 24, 32, and 34, by inserting a detection probe 172 into the vessel 80 via the vessel port 92 and detecting the condition of the vessel interior surface 88 or a barrier or other type of coating 90 using the probe 172. Inspecting can be carried out, as shown in FIG. 5, by radiating energy inward through the vessel wall 86 and vessel interior surface 88 and detecting the energy with the probe 172. Or, inspecting can be carried out by reflecting the radiation from the vessel interior surface 88 and detecting the energy with a detector located inside the vessel 80. Or, inspecting can be carried out by detecting the condition of the vessel interior surface 88 at numerous, closely spaced positions on the vessel interior surface.

Any of the above methods can include carrying out the inspecting step at a sufficient number of positions throughout the vessel interior surface 88 to determine that the barrier or other type of coating 90 will be effective to prevent the pressure within the vessel, when it is initially evacuated and its wall is exposed to the ambient atmosphere, from increasing to more than 20% of the ambient atmospheric pressure during a shelf life of a year.

Any of the above methods can include carrying out the inspecting step within an elapsed time of 30 or fewer seconds per vessel, or 25 or fewer seconds per vessel, or 20 or fewer seconds per vessel, or 15 or fewer seconds per vessel, or 10 or fewer seconds per vessel, or 5 or fewer seconds per vessel, or 4 or fewer seconds per vessel, or 3 or fewer seconds per vessel, or 2 or fewer seconds per vessel, or 1 or fewer seconds per vessel. This can be made possible, for example, by measuring the efficacy of the barrier or other type of coated vessel wall, which can include one measurement for the entire vessel 80, or by inspecting many or even all the points to be inspected in parallel, as by using the charge coupled device as the detector 172 shown or substitutable in FIGS. 3-5. The latter step can be used for detecting the condition of the barrier or other type of coating at numerous, closely spaced positions on the vessel interior surface 88 in a very short overall time.

In any embodiment of the method, a multi-point vessel inspection can be further expedited, if desired, by collecting data using a charge coupled device 172, transporting away the vessel 80 that has just been inspected, and processing the collected data shortly thereafter, while the vessel 80 is moving downstream. If a defect in the vessel 80 is later ascertained due to the data processing, the vessel 80 that is defective can be moved off line at a point downstream of the detection station such as 34 (FIG. 4).

In any of the above embodiments, the inspecting step can be carried out at a sufficient number of positions throughout the vessel 80 interior surface 88 to determine that the barrier or other type of coating 90 will be effective to prevent the initial vacuum level (i.e. initial reduction of pressure versus ambient) within the vessel 80, when it is initially evacuated and its wall 86 is exposed to the ambient atmosphere, from decreasing more than 20%, optionally more than 15%, optionally more than 10%, optionally more than 5%, optionally more than 2%, during a shelf life of at least 12 months, or at least 18 months, or at least two years.

The initial vacuum level can be a high vacuum, i.e. a remaining pressure of less than 10 Torr, or a lesser vacuum such as less than 20 Torr of positive pressure (i.e. the excess pressure over a full vacuum), or less than 50 Torr, or less than 100 Torr, or less than 150 Torr, or less than 200 Torr, or less than 250 Torr, or less than 300 Torr, or less than 350 Torr, or less than 380 Torr of positive pressure. The initial vacuum level of evacuated blood collection tubes, for example, is in many instances determined by the type of test the tube is to be used for, and thus the type and appropriate amount of a reagent that is added to the tube at the time of manufacture. The initial vacuum level is commonly set to draw the correct volume of blood to combine with the reagent charge in the tube.

In any of the above embodiments, the barrier or other type of coating 90 inspecting step can be carried out at a sufficient number of positions throughout the vessel interior surface 88 to determine that the barrier or other type of coating 90 will be effective to prevent the pressure within the vessel 80, when it is initially evacuated and its wall is exposed to the ambient atmosphere, from increasing to more than 15%, or more than 10%, of the ambient atmospheric pressure of the ambient atmospheric pressure during a shelf life of at least one year.

In the embodiment of FIGS. 1 and 4, the processing station or device 34 can be another optical inspection, this time intended to scan or separately measure the properties of at least a portion of the barrier or other type of coating 90, or substantially the entire barrier or other type of coating 90, at numerous, closely spaced positions on the barrier or other type of coating 90. The numerous, closely spaced positions can be, for example, spaced about 1 micron apart, or about 2 microns apart, or about 3 microns apart, or about 4 microns apart, or about 5 microns apart, or about 6 microns apart, or about 7 microns apart, either in every case or on average over at least part of the surface, thus separately measuring some or all small portions of the barrier or other type of coating 90. In an embodiment, a separate scan of each small area of the coating can be useful to find individual pinholes or other defects, and to distinguish the local effects of pinhole defects from more general defects, such as a large area with a coating that is too thin or porous.

The inspection by the station or device 34 can be carried out by inserting a radiation or light source 170 or any other suitable radio frequency, microwave, infrared, visible light, ultraviolet, x-ray, or electron beam source, for example, into the vessel 80 via the vessel port 92 and detecting the condition of the vessel interior surface, for example the barrier coating 90, by detecting radiation transmitted from the radiation source using a detector.

The above vessel holder system can also be used for testing the device. For example, the probe 108 of FIG. 2 having a gas delivery port 110 can be replaced by a light source 170 (FIG. 4). The light source 170 can irradiate the inside of the tube and then subsequent testing can be completed outside of the tube, measuring transmission or other properties. The light source 170 can be extended into the inside of the tube in the same manner that the probe 108 is pushed into the puck or vessel holder 62, although a vacuum and seals are not necessarily required. The light source 170 can be an optical fiber source, a laser, a point (such as an LED) source or any other radiation source. The source can radiate at one or more frequencies from the deep UV (100 nm) into the far infra-red (100 microns) and all frequencies in between. There is no limitation on the source that can be used.

As a specific example see FIG. 4. In FIG. 4 the tube or vessel 80 is positioned in the puck or vessel holder 62 and a light source 170 at the end of the probe 108 has been inserted into the tube. The light source 170 in this case can be a blue LED source of sufficient intensity to be received by the detector 172 surrounding the outside of the vessel 80. The light source 170 can be, for example, a three dimensional charge-coupled-device (CCD) comprising an array of pixels such as 174 on its interior surface 176. The pixels such as 174 receive and detect the illumination radiated through the barrier or other type of coating 90 and vessel wall 86. In this embodiment the detector 172 has a larger inner diameter relative to the vessel 80 than the separation of the electrode 164 and vessel 80 of FIG. 2, and has a cylindrical top portion adjacent to the closed end 84 instead of a hemispherical top portion. The outside detector 172 or can have a smaller radial gap from the vessel 80 and a gap of more uniform dimension at its top portion adjacent to the closed end 84. This can be accomplished, for example, by providing a common center of curvature for the closed end 84 and the top of the detector 172 when the vessel 80 is seated. This variation might provide more uniform inspection of the curved closed end 84 of the vessel 80, although either variation is contemplated to be suitable.

Prior to the light source being turned on, the CCD is measured and the resulting value stored as a background (which can be subtracted from subsequent measurements). The light source 170 is then turned on and measurements taken with the CCD. The resulting measurements can then be used to compute total light transmission (and compared to an uncoated tube to determine the average coating thickness) and defect density (by taking individual photon counts on each element of the CCD and comparing them to a threshold value—if the photon count is lower, then this corresponds to not enough light being transmitted). Low light transmission likely is the result of no or too-thin coating—a defect in the coating on the tube. By measuring the number of adjacent elements that have a low photon count, the defect size can be estimated. By summing the size and number of defects, the tube's quality can be assessed, or other properties determined that might be specific to the frequency of the radiation from the light source 170.

In the embodiment of FIG. 4, energy can be radiated outward through the vessel interior surface, such as through the coating 90 and the vessel wall 86, and detected with a detector 172 located outside the vessel. Various types of detectors 172 can be used.

Since the incident radiation from the source 170 transmitted through the barrier or other type of coating 90 and vessel wall 80 can be greater for a lower angle of incidence (compared to a reference line normal to the vessel wall 80 at any given point), the pixels such as 174 lying on a normal line through the vessel wall 86 will receive more of the radiation than neighboring pixels, though more than one pixel can receive some of the light passing through a given portion of the barrier or other type of coating, and the light passing through more than one given portion of the barrier or other type of coating 90 and vessel wall 80 will be received by a particular pixel such as 174.

The degree of resolution of the pixels such as 174 for detecting radiation passing through a particular portion of the barrier or other type of coating 90 and vessel wall 86 can be increased by placing the CCD so its array of pixels such as 174 is very close to and closely conforms to the contours of the vessel wall 86. The degree of resolution can also be increased by selecting a smaller or essentially point source of light, as shown diagrammatically in FIG. 3, to illuminate the interior of the vessel 80. Using smaller pixels will also improve the resolution of the array of pixels in the CCD.

Figure 6:
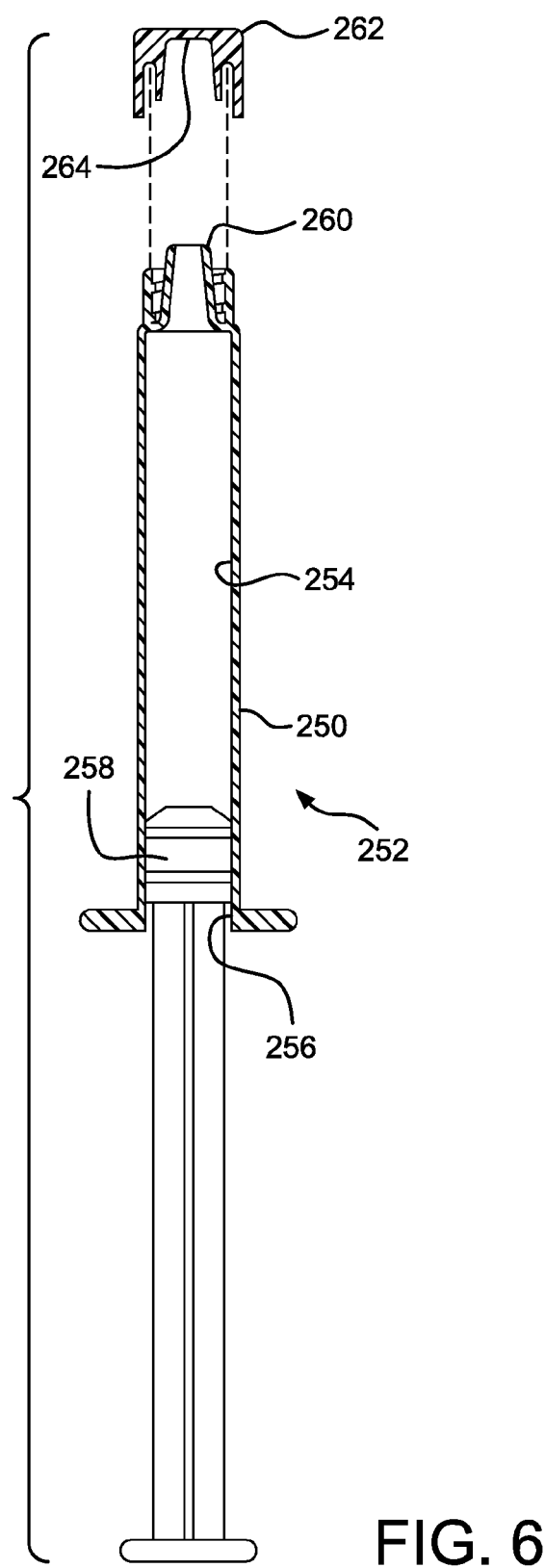
FIG. 6 is an exploded longitudinal sectional view of a syringe and cap adapted for use as a prefilled syringe.
Figure 7:
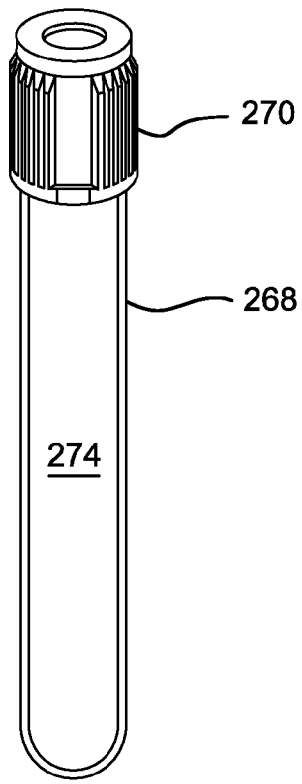
FIG. 7 is a perspective view of a blood collection tube assembly having a closure according to still another embodiment of the disclosure.
Figure 8:
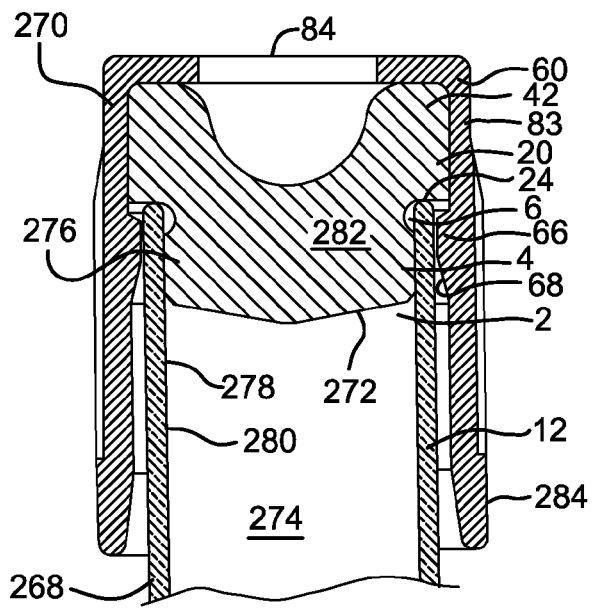
FIG. 8 is a fragmentary section of the blood collection tube and closure assembly of FIG. 7.
Figure 9:
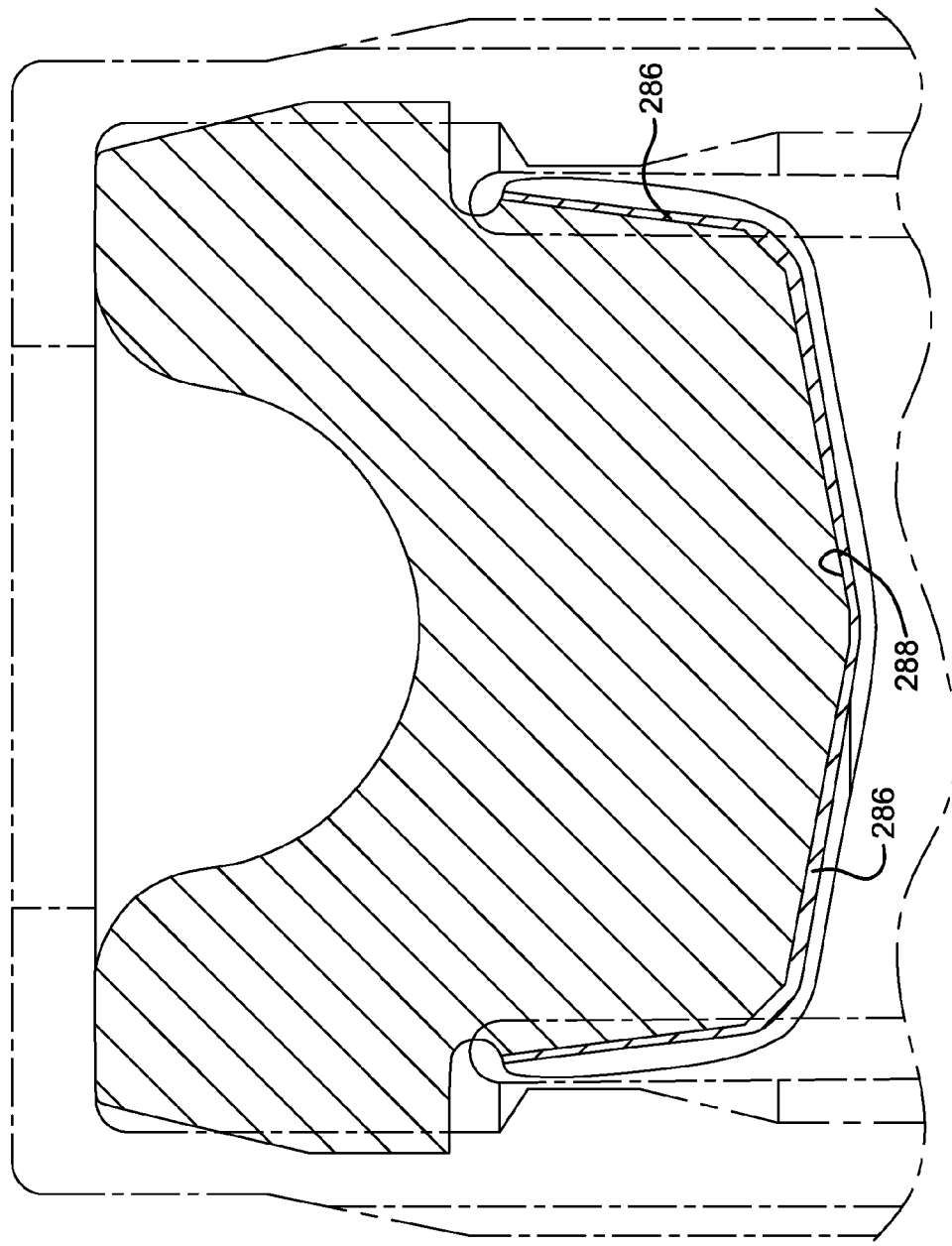
FIG. 9 is an isolated section of an elastomeric insert of the closure of FIGS. 7 and 8.

In FIG. 6 a point light source 132 (laser or LED) is positioned at the end of a rod or probe. ("Point source" refers either to light emanating from a small-volume source resembling a mathematical point, as can be generated by a small LED or a diffusing tip on an optical fiber radiating light in all directions, or to light emanated as a small-cross-section beam, such as coherent light transmitted by a laser.) The point source of light 132 can be either stationary or movable, for example axially movable, while the characteristics of the barrier or other type of coating 90 and vessel wall 80 are being measured. If movable, the point light source 132 can be moved up and down inside of the device (tube) 80. In a similar manner described above, the interior surface 88 of the vessel 80 can be scanned and subsequent measurements made by an external detector apparatus 134 to determine coating integrity. An advantage of this approach is that a linearly polarized or similar coherent light source with specific directionality can be used.

The position of the point source of light 132 can be indexed to the pixels such as 174 so the illumination of the detectors can be determined at the time the detector is at a normal angle with respect to a particular area of the coating 90. In the embodiment of FIG. 4, a cylindrical detector 172, optionally with a curved end matching the curve (if any) of the closed end 84 of a vessel 80, can be used to detect the characteristics of a cylindrical vessel 80.

It will be understood, with reference to FIG. 4, that the inspection station or device 24 or 34 can be modified by reversing the positions of the light or other radiation source 170 and detector 172 so the light radiates through the vessel wall 86 from the exterior to the interior of the vessel 80. If this expedient is selected, in an embodiment a uniform source of incident light or other radiation can be provided by inserting the vessel 80 into an aperture 182 through the wall 184 of an integrating sphere light source 186. An integrating sphere light source will disperse the light or radiation from the source 170 outside the vessel 80 and inside the integrating sphere, so the light passing through the respective points of the wall 86 of the vessel 80 will be relatively uniform. This will tend to reduce the distortions caused by artifacts relating to portions of the wall 86 having different shapes.

In the embodiment of FIG. 5, the detector 172 can be shown to closely conform to the barrier or other type of coating 90 or interior surface 88 of the vessel 80. Since the detector 172 can be on the same side of the vessel wall 86 as the barrier or other type of coating 80, this proximity will tend to increase the resolution of the pixels such as 174, though in this embodiment the detector 172 optionally will be precisely positioned relative to the barrier or other type of coating 90 to avoid scraping one against the other, possibly damaging either the coating or the CCD array. Placing the detector 172 immediately adjacent to the coating 90 also can reduce the effects of refraction by the vessel wall 86, which in the embodiment of FIG. 4 occurs after the light or other radiation passes through the barrier or other type of coating 90, so the signal to be detected can be differentially refracted depending on the local shape of the vessel 80 and the angle of incidence of the light or other radiation.

Other barrier or other type of coating inspection techniques and devices can also, or, be used. For example, fluorescence measurements can be used to characterize the treatment/coating on the device. Using the same apparatus described in FIGS. 4 and 6, a light source 132 or 170 (or other radiation source) can be selected that can interact with the polymer material of the wall 86 and/or a dopant in the polymer material of the wall 86. Coupled with a detection system, this can be used to characterize a range of properties including defects, thicknesses and other performance factors.

Yet another example of inspection is to use x-rays to characterize the treatment/coating and/or the polymer itself. In FIG. 3 or 4, the light source can be replaced with an x-radiation source and the external detector can be of a type to measure the x-ray intensity. Elemental analysis of the barrier or other type of coating can be carried out using this technique.

After molding a device 80, as at the station 22, several potential issues can arise that will render any subsequent treatment or coating imperfect, and possibly ineffective. If the devices are inspected prior to coating for these issues, the devices can be coated with a highly optimized, optionally up to 6-sigma controlled process that will ensure a desired result (or results).

Some of the potential problems that can interfere with treatment and coating include (depending on the nature of the coated article to be produced):

1. Large density of particulate contamination defects (for example, each more than 10 micrometers in its longest dimension), or a smaller density of large particulate contamination (for example, each more than 10 micrometers in its longest dimension).

2. Chemical or other surface contamination (for example silicone mold release or oil).

3. High surface roughness, characterized by either a high/large number of sharp peaks and/or valleys. This can also be characterized by quantifying the average roughness (Ra) which should be less than 100 nm.

4. Any defect in the device such as a hole that will not allow a vacuum to be created.

5. Any defect on the surface of the device that will be used to create a seal (for example the open end of a sample collection tube).

6. Large wall thickness non-uniformities which can impede or modify power coupling through the thickness during treatment or coating.

7. Other defects that will render the barrier or other type of coating ineffective.

To assure that the treatment/coating operation is successful using the parameters in the treatment/coating operation, the device can be pre-inspected for one or more of the above potential issues or other issues. Previously, an apparatus was disclosed for holding a device (a puck or vessel holder such as 38-68) and moving it through a production process, including various tests and a treatment/coating operation. Several possible tests can be implemented to ensure that a device will have the appropriate surface for treatment/coating. These include:

1. Optical Inspection, for example, transmission of radiation through the device, reflection of radiation from the inside of the device or from the outside, absorption of radiation by the device, or interference with radiation by the device.

2. Digital Inspection—for example, using a digital camera that can measure specific lengths and geometries (for example how "round" or otherwise evenly or correctly shaped the open end of a sample collection tube is relative to a reference).

3. Vacuum leak checking or pressure testing.

4. Sonic (ultrasonic) testing of the device.

5. X-ray analysis.

6. Electrical conductivity of the device (the plastic tube material and $SiO_x$ have different electrical resistance—on the order of 1020 Ohm-cm for quartz as a bulk material and on the order of 1014 Ohm-cm for polyethylene terephthalate, for example).

7. Thermal conductivity of the device (for example, the thermal conductivity of quartz as a bulk material is about 1.3 W-° K/m, while the thermal conductivity of polyethylene terephthalate is 0.24 W-° K/m).

8. Outgassing of the vessel wall, which optionally can be measured as described below under post-coating inspection to determine an outgassing baseline.

The above testing can be conducted in a station 24 as shown in FIG. 3. In this figure the device (for example a sample collection tube 80) can be held in place and a light source (or other source) 132 can be inserted into the device and an appropriate detector 134 positioned outside of the device to measure the desired result.

In the case of vacuum leak detection, the vessel holder and device can be coupled to a vacuum pump and a measuring device inserted into the tube. The testing can also be conducted as detailed elsewhere in the specification.

The processing station or device 24 can be a visual inspection station, and can be configured to inspect one or more of the interior surface 88 of a vessel, its exterior surface 118, or the interior of its vessel wall 86 between its surfaces 88 and 118 for defects. The inspection of the exterior surface 118, the interior surface 88, or the vessel wall 86 can be carried out from outside the vessel 80, particularly if the vessel is transparent or translucent to the type of radiation and wavelength used for inspection. The inspection of the interior surface 88 can or be facilitated, if desired, by providing an optical fiber probe inserted into the vessel 80 via the vessel port 92, so a view of the inside of the vessel 80 can be obtained from outside the vessel 80. An endoscope or borescope can be used in this environment, for example.

Another expedient illustrated in FIG. 3 can be to insert a light source 132 within a vessel 80. The light transmitted through the vessel wall 86, and artifacts of the vessel 80 made apparent by the light, can be detected from outside the vessel 80, as by using a detector measuring apparatus 134.

This station or device 24 can be used, for example, to detect and correct or remove misaligned vessels 80 not properly seated on the vessel port 96 or vessels 80 that have a visible distortion, impurity, or other defect in the wall 86. Visual inspection of the vessel 80 also can be conducted by a worker viewing the vessel 80, instead or in addition to machine inspection.

The processing station or device 26 can be optionally configured to inspect the interior surface 88 of a vessel 80 for defects, and for example to measure the gas pressure loss through the vessel wall 86, which can be done before a barrier or other type of coating is provided. This test can be carried out by creating a pressure difference between the two sides of the barrier coating 90, as by pressurizing or evacuating the interior of the vessel 80, isolating the interior 154 of the vessel 80 so the pressure will remain constant absent leakage around the seal or permeation of gas through the vessel wall, and measuring the pressure change per unit time accumulating from these problems. This measurement will not only reveal any gas coming through the vessel wall 86, but will also detect a leaking seal between the mouth 82 of the vessel and the O-ring or other seal 100, which might indicate either a problem with the alignment of the vessel 80 or with the function of the seal 100. In either case, the tube mis-seating can be corrected or the tube taken out of the processing line, saving time in attempting to achieve or maintain the proper processing vacuum level and preventing the dilution of the process gases by air drawn through a malfunctioning seal.

The above systems can be integrated into a manufacturing and inspection method comprising multiple steps.

FIG. 1 as previously described shows a schematic layout of the steps of one possible method (although this disclosure is not limited to a single concept or approach). First the vessel 80 is visually inspected at the station or by the device 24, which can include dimensional measurement of the vessel 80. If there are any defects found, the device or vessel 80 is rejected and the puck or vessel holder such as 38 is inspected for defects, recycled or removed.

Next the leak rate or other characteristics of the assembly of a vessel holder 38 and seated vessel 80 is tested, as at the station 26, and stored for comparison after coating. The puck or vessel holder 38 then moves, for example, into the coating step 28. The device or vessel 80 is coated with a $SiO_x$ or other barrier or other type of coating at a power supply frequency of, for example, 13.56 MHz. Once coated, the vessel holder is retested for its leak rate or other characteristics (this can be carried out as a second test at the testing station 26 or a duplicate or similar station such as 30—the use of a duplicate station can increase the system throughput).

The coated measurement can be compared to the uncoated measurement. If the ratio of these values exceeds a pre-set required level, indicating an acceptable overall coating performance, the vessel holder and device move on. An alternative optical testing station 32, for example, follows with a blue light source and an external integrating sphere detector to measure the total light transmitted through the tube. The value can be required to exceed a pre-set limit at which the device is rejected or recycled for additional coating. Next (for devices that are not rejected), a second optical testing station 34 can be used. In this case a point light source can be inserted inside of the tube or vessel 80 and pulled out slowly while measurements are taken with a tubular CCD detector array outside of the tube. The data is then computationally analyzed to determine the defect density distribution. Based on the measurements the device is either approved for final packaging or rejected.

The above data optionally can be logged and plotted (for example, electronically) using statistical process control techniques to ensure up to 6-sigma quality.

PECVD Treated Vessels

Vessels are contemplated having a barrier coating 90 (shown in FIG. 2, for example), which can be an $SiO_x$ coating applied to a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. Additionally contemplated ranges are 1 to 5000 nm, or 10 to 1000 nm, or 10-200 nm, or 20 to 100 nm thick.

The composition (except hydrogen) of the $SiO_x$ or other coating can be measured, for example, by X-ray photoelectron spectroscopy (XPS).

A composite coating can be used, such as a carbon-based coating combined with $SiO_x$. This can be done, for example, by changing the reaction conditions or by adding a substituted or unsubstituted hydrocarbon, such as an alkane, alkene, or alkyne, to the feed gas as well as an organosilicon-based compound. See for example U.S. Pat. No. 5,904,952, which states in relevant part: "For example, inclusion of a lower hydrocarbon such as propylene provides carbon moieties and improves most properties of the deposited films (except for light transmission), and bonding analysis indicates the film to be silicon dioxide in nature. Use of methane, methanol, or acetylene, however, produces films that are silicone in nature. The inclusion of a minor amount of gaseous nitrogen to the gas stream provides nitrogen moieties in the deposited films and increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness."

A diamond-like carbon (DLC) coating can be formed as the primary or sole coating deposited. This can be done, for example, by changing the reaction conditions or by feeding methane, hydrogen, and helium to a PECVD process. These reaction feeds have no oxygen, so no OH moieties can be formed. For one example, an $SiO_x$ coating can be applied on the interior of a tube or syringe barrel and an outer DLC coating can be applied on the exterior surface of a tube or syringe barrel. Or, the $SiO_x$ and DLC coatings can both be applied as a single layer or plural layers of an interior tube or syringe barrel coating.

Referring to FIG. 2, the barrier or other type of coating 90 reduces the transmission of atmospheric gases into the vessel 80 through its interior surface 88. Or, the barrier or other type of coating 90 reduces the contact of the contents of the vessel 80 with the interior surface 88. The barrier or other type of coating can comprise, for example, $SiO_x$, amorphous (for example, diamond-like) carbon, or a combination of these.

Any coating described herein can be used for coating a surface, for example a plastic surface. It can further be used as a barrier layer, for example as a barrier against a gas or liquid, optionally against water vapor, oxygen and/or air. It can also be used for preventing or reducing mechanical and/or chemical effects which the coated surface would have on a compound or composition if the surface were uncoated. For example, it can prevent or reduce the precipitation of a compound or composition, for example insulin precipitation or blood clotting or platelet activation.

B. Syringes

The foregoing description has largely addressed applying a barrier coating to a tube with one permanently closed end, such as a blood collection tube or, more generally, a specimen receiving tube 80. The apparatus is not limited to such a device.

Figure 20:
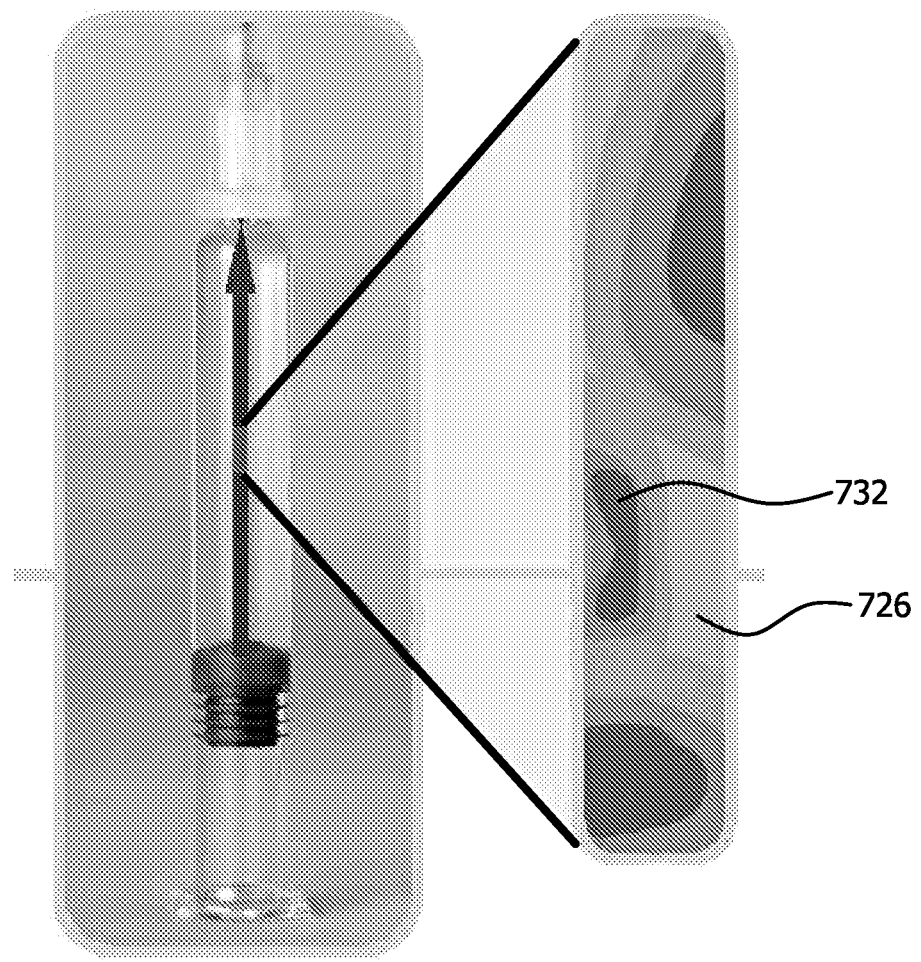
FIG. 20 is a more detailed view of the map 726 of FIG. 19.
Figure 21:
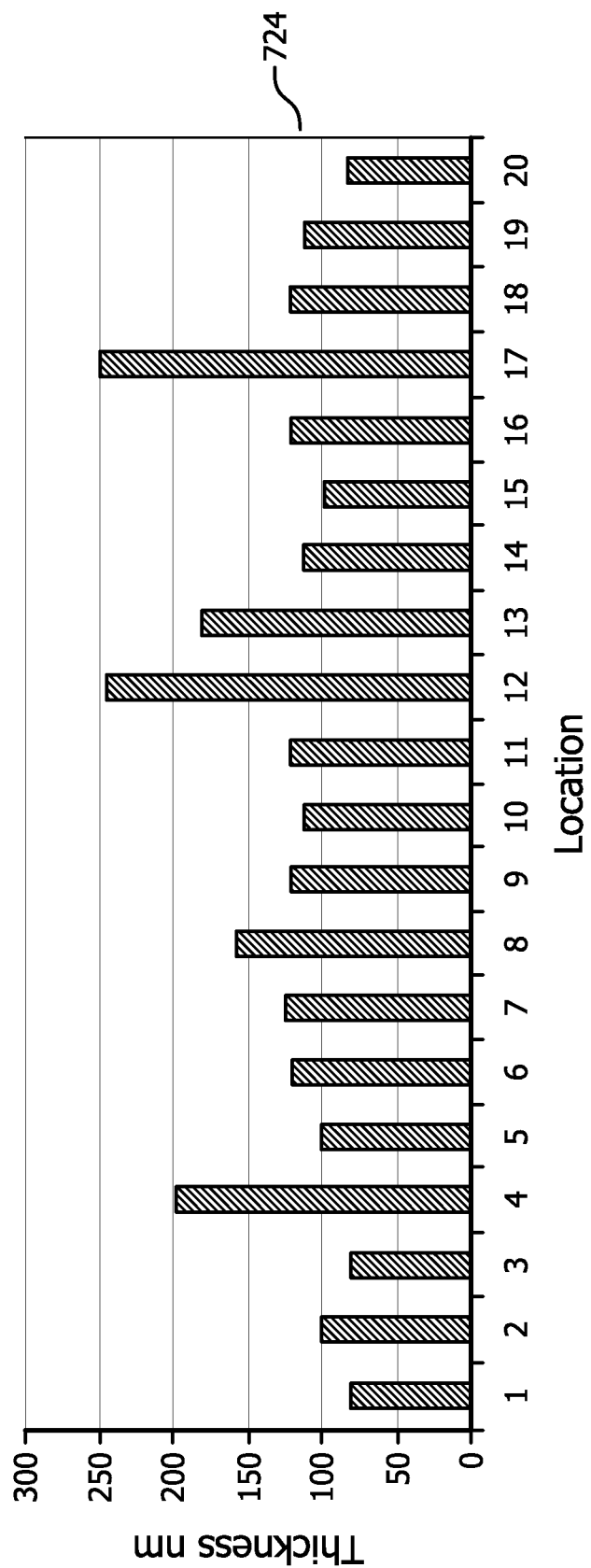
FIG. 21 is a more detailed view of the map 724 of FIG. 19.

Another example of a suitable vessel, shown in FIGS. 20-22, is a syringe barrel 250 for a medical syringe 252. Such syringes 252 are sometimes supplied prefilled with saline solution, a pharmaceutical preparation, or the like for use in medical techniques. Pre-filled syringes 252 are also contemplated to benefit from an $SiO_x$ barrier or other type of coating on the interior surface 254 to keep the contents of the prefilled syringe 252 out of contact with the plastic of the syringe, for example of the syringe barrel 250 during storage. The barrier or other type of coating can be used to avoid leaching components of the plastic into the contents of the barrel through the interior surface 254.

A syringe barrel 250 as molded commonly can be open at both the back end 256, to receive a plunger 258, and at the front end 260, to receive a hypodermic needle, a nozzle, or tubing for dispensing the contents of the syringe 252 or for receiving material into the syringe 252. But the front end 260 can optionally be capped and the plunger 258 optionally can be fitted in place before the prefilled syringe 252 is used, closing the barrel 250 at both ends. A cap 262 can be installed either for the purpose of processing the syringe barrel 250 or assembled syringe, or to remain in place during storage of the prefilled syringe 252, up to the time the cap 262 is removed and (optionally) a hypodermic needle or other delivery conduit is fitted on the front end 260 to prepare the syringe 252 for use.

B.1. Assemblies

Figure 15:
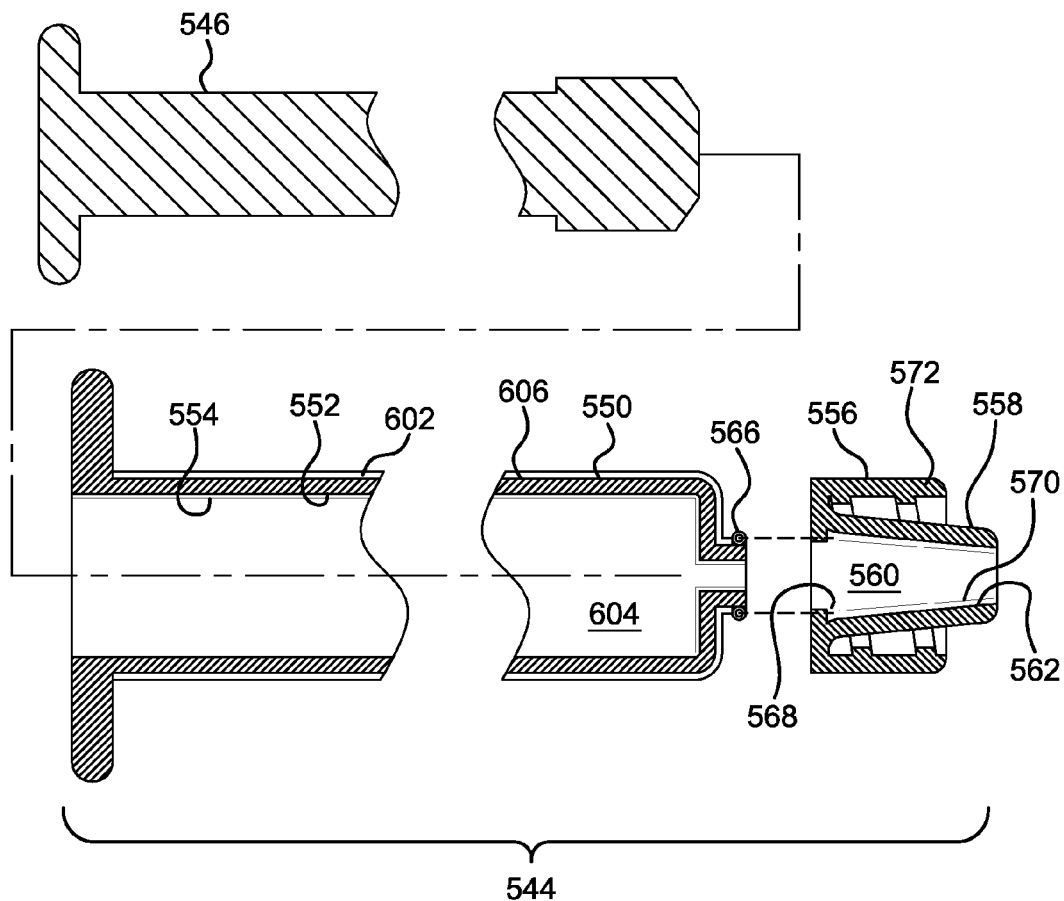
FIG. 15 is an exploded view of a two-piece syringe barrel and Luer lock fitting. The syringe barrel is usable with the vessel treatment and inspection apparatus of FIGS. 1-6.
Figure 16:
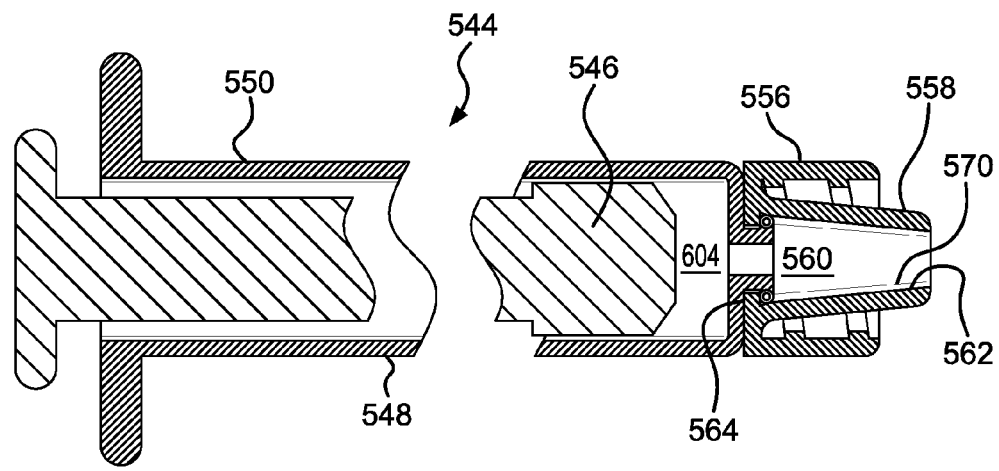
FIG. 16 is an assembled view of the two-piece syringe barrel and Luer lock fitting of FIG. 15.

FIG. 15 is an exploded view and FIG. 16 is an assembled view of a syringe. The syringe barrel can be processed with the vessel treatment and inspection apparatus of FIGS. 1-6, for example.

The installation of a cap 262 makes the barrel 250 a closed-end vessel that can be provided with an $SiO_x$ barrier or other type of coating on its interior surface 254 in the previously illustrated apparatus, optionally also providing a coating on the interior 264 of the cap and bridging the interface between the cap interior 264 and the barrel front end 260. Suitable apparatus adapted for this use is analogous to FIG. 2 except for the substitution of the capped syringe barrel 250 for the vessel 80 of FIG. 2.

Protocol for Coating COC Syringe Barrel Interior with $SiO_x$ (Used, e.g. in Example 8 and Station 28.)

An injection molded COC syringe barrel was interior coated with SiOx. The apparatus as shown in FIG. 2 was modified to hold a COC syringe barrel with butt sealing at the base of the COC syringe barrel. Additionally a cap was fabricated out of a stainless steel Luer fitting and a polypropylene cap that sealed the end of the COC syringe barrel, allowing the interior of the COC syringe barrel to be evacuated.

The vessel holder 50 was made from Delrin® with an outside diameter of 1.75 inches (44 mm) and a height of 1.75 inches (44 mm). The vessel holder 50 was housed in a Delrin® structure that allowed the device to move in and out of the electrode 160.

The electrode 160 was made from copper with a Delrin® shield. The Delrin® shield was conformal around the outside of the copper electrode 160. The electrode 160 measured approximately 3 inches (76 mm) high (inside) and was approximately 0.75 inches (19 mm) wide. The COC syringe barrel was inserted into the vessel holder 50, base sealing with an Viton® O-rings.

The COC syringe barrel was carefully moved into the sealing position over the extended (stationary) ⅛-inch (3-mm.) diameter brass probe or counter electrode 108 and pushed against a copper plasma screen. The copper plasma screen was a perforated copper foil material (K&S Engineering Part #LXMUW5 Copper mesh) cut to fit the outside diameter of the COC syringe barrel and was held in place by a abutment surface 494 that acted as a stop for the COC syringe barrel insertion. Two pieces of the copper mesh were fit snugly around the brass probe or counter electrode 108 insuring good electrical contact.

The probe or counter electrode 108 extended approximately 20 mm into the interior of the COC syringe barrel and was open at its end. The brass probe or counter electrode 108 extended through a Swagelok® fitting located at the bottom of the vessel holder 50, extending through the vessel holder 50 base structure. The brass probe or counter electrode 108 was grounded to the casing of the RF matching network.

The gas delivery port 110 was connected to a stainless steel assembly comprised of Swagelok® fittings incorporating a manual ball valve for venting, a thermocouple pressure gauge and a bypass valve connected to the vacuum pumping line. In addition, the gas system was connected to the gas delivery port 110 allowing the process gases, oxygen and hexamethyldisiloxane (HMDSO) to be flowed through the gas delivery port 110 (under process pressures) into the interior of the COC syringe barrel.

The gas system was comprised of a Aalborg® GFC17 mass flow meter (Cole Parmer Part # EW-32661-34) for controllably flowing oxygen at 90 sccm (or at the specific flow reported for a particular example) into the process and a PEEK capillary (OD 1/16-inch (3-mm) ID 0.004 inches (0.1 mm)) of length 49.5 inches (1.26 m). The PEEK capillary end was inserted into liquid hexamethyldisiloxane (Alfa Aesar® Part Number L16970, NMR Grade). The liquid HMDSO was pulled through the capillary due to the lower pressure in the COC syringe barrel during processing. The HMDSO was then vaporized into a vapor at the exit of the capillary as it entered the low pressure region.

To ensure no condensation of the liquid HMDSO past this point, the gas stream (including the oxygen) was diverted to the pumping line when it was not flowing into the interior of the COC syringe barrel for processing via a Swagelok® 3-way valve.

Once the COC syringe barrel was installed, the vacuum pump valve was opened to the vessel holder 50 and the interior of the COC syringe barrel. An Alcatel rotary vane vacuum pump and blower comprised the vacuum pump system. The pumping system allowed the interior of the COC syringe barrel to be reduced to pressure(s) of less than 150 mTorr while the process gases were flowing at the indicated rates. A lower pumping pressure was achievable with the COC syringe barrel, as opposed to the tube, because the COC syringe barrel has a much smaller internal volume.

After the base vacuum level was achieved, the vessel holder 50 assembly was moved into the electrode 160 assembly. The gas stream (oxygen and HMDSO vapor) was flowed into the brass gas delivery port 110 (by adjusting the 3-way valve from the pumping line to the gas delivery port 110). The pressure inside the COC syringe barrel was approximately 200 mTorr as measured by a capacitance manometer (MKS) installed on the pumping line near the valve that controlled the vacuum. In addition to the COC syringe barrel pressure, the pressure inside the gas delivery port 110 and gas system was also measured with the thermocouple vacuum gauge that was connected to the gas system. This pressure was typically less than 8 Torr.

When the gas was flowing to the interior of the COC syringe barrel, the RF power supply was turned on to its fixed power level. A ENI ACG-6 600 Watt RF power supply was used (at 13.56 MHz) at a fixed power level of approximately 30 Watts. The RF power supply was connected to a COMDEL CPMX1000 auto match that matched the complex impedance of the plasma (to be created in the COC syringe barrel) to the 50 ohm output impedance of the ENI ACG-6 RF power supply. The forward power was 30 Watts (or whatever value is reported in a working example) and the reflected power was 0 Watts so that the power was delivered to the interior of the COC syringe barrel. The RF power supply was controlled by a laboratory timer and the power on time set to 5 seconds (or the specific time period reported for a particular example).

Upon initiation of the RF power, a uniform plasma was established inside the interior of the COC syringe barrel. The plasma was maintained for the entire 5 seconds (or other coating time indicated in a specific example) until the RF power was terminated by the timer. The plasma produced a silicon oxide coating of approximately 20 nm thickness (or the thickness reported in a specific example) on the interior of the COC syringe barrel surface.

After coating, the gas flow was diverted back to the vacuum line and the vacuum valve was closed. The vent valve was then opened, returning the interior of the COC syringe barrel to atmospheric pressure (approximately 760 Torr). The COC syringe barrel was then carefully removed from the vessel holder 50 assembly (after moving the vessel holder 50 assembly out of the electrode 160 assembly).

EXAMPLES

Example 1

Interference Patterns from Reflectance Measurements—Prophetic Example

Using a UV-Visible Source (Ocean Optics DH2000-BAL Deuterium Tungsten 200-1000 nm), a fiber optic reflection probe (combination emitter/collector Ocean Optics QR400-7 SR/BX with approximately 3 mm probe area), miniature detector (Ocean Optics HR4000CG UV-NIR Spectrometer), and software converting the spectrometer signal to a transmittance/wavelength graph on a laptop computer, an uncoated PET tube Becton Dickinson (Franklin Lakes, N.J., USA) Product No. 366703 13×75 mm (no additives) is scanned (with the probe emitting and collecting light radially from the centerline of the tube, thus normal to the coated surface) both about the inner circumference of the tube and longitudinally along the inner wall of the tube, with the probe, with no observable interference pattern observed.

Then a Becton Dickinson Product No. 366703 13×75 mm (no additives) $SiO_x$ plasma-coated BD 366703 tube is coated with a 20 nanometer thick $SiO_2$ coating as described in Protocol for Coating Tube Interior with $SiO_x$. This tube is scanned in a similar manner as the uncoated tube. A clear interference pattern is observed with the coated tube, in which certain wavelengths were reinforced and others canceled in a periodic pattern, indicating the presence of a coating on the PET tube.

Example 2

Enhanced Light Transmission from Integrating Sphere Detection

The equipment used was a Xenon light source (Ocean Optics HL-2000-HP-FHSA—20 W output Halogen Lamp Source (185-2000 nm)), an Integrating Sphere detector (Ocean Optics ISP-80-8-I) machined to accept a PET tube into its interior, and HR2000+ES Enhanced Sensitivity UV.VIS spectrometer, with light transmission source and light receiver fiber optic sources (QP600-2-UV-VIS—600 um Premium Optical FIBER, UV/VIS, 2 m), and signal conversion software (SP ECTRASUITE—Cross-platform Spectroscopy Operating SOFTWARE). An uncoated PET tube made according to the Protocol for Forming PET Tube was inserted onto a TEFZEL Tube Holder (Puck), and inserted into the integrating sphere. With the Spectrasuite software in absorbance mode, the absorption (at 615 nm) was set to zero. An $SiO_x$ coated tube made according to the Protocol for Forming PET Tube and coated according to the Protocol for Coating Tube Interior with $SiO_x$ (except as varied in Table 1) was then mounted on the puck, inserted into the integrating sphere and the absorbance recorded at 615 nm wavelength. The data is recorded in Table 1.

With the $SiO_x$ coated tubes, an increase in absorption relative to the uncoated article was observed; increased coating times resulted in increased absorption. The measurement took less than one second.

These spectroscopic methods should not be considered limited by the mode of collection (for example, reflectance vs. transmittance vs. absorbance), the frequency or type of radiation applied, or other parameters.

Example 3

Outgassing Measurement on PET

Figure 11:
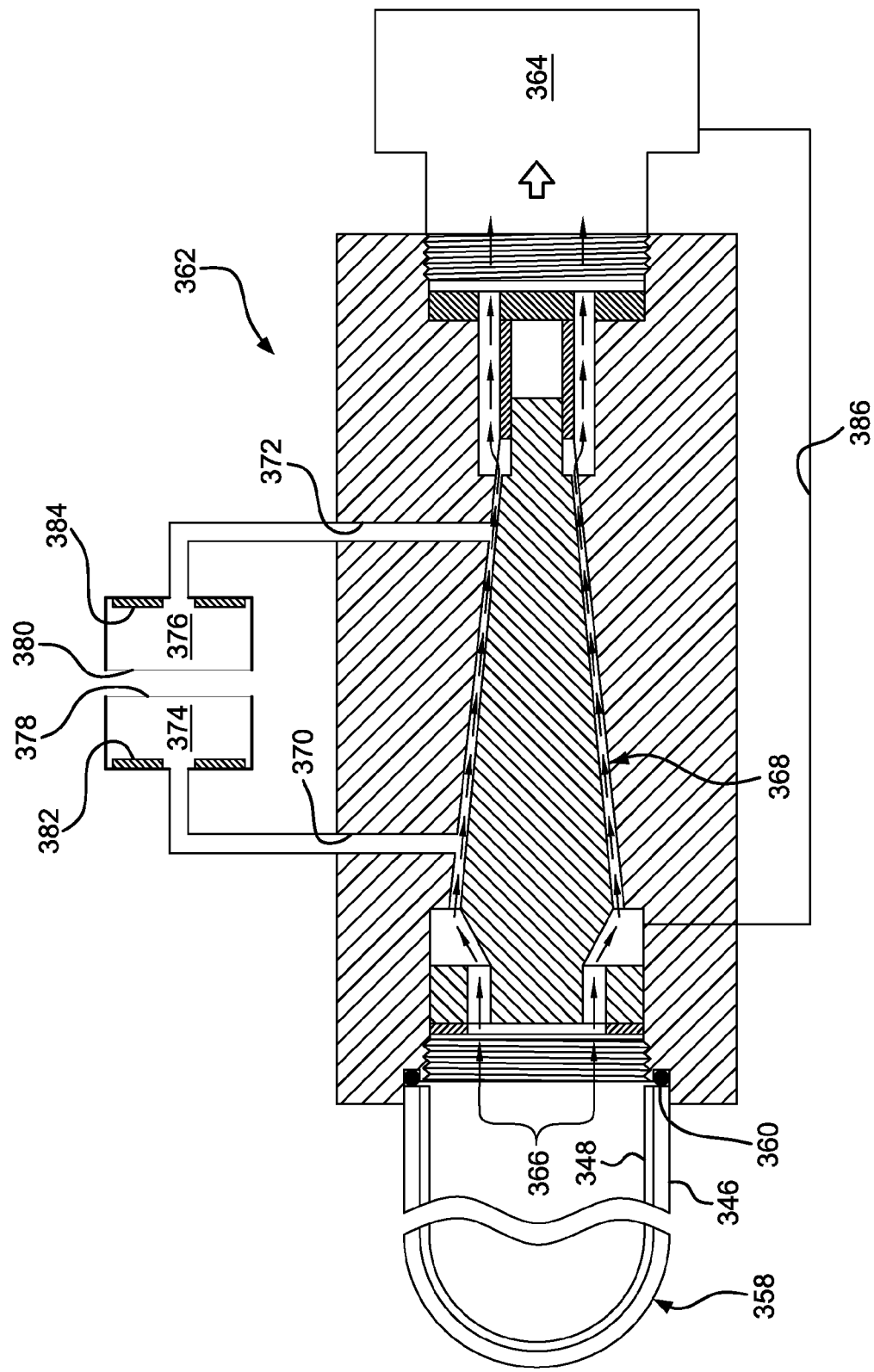
FIG. 11 is a schematic sectional view of a test set-up for causing outgassing of the wall of a vessel to the interior of the vessel and measurement of the outgassing using a measurement cell interposed between the vessel and a source of vacuum.

Present FIG. 11, adapted from FIG. 15 of U.S. Pat. No. 6,584,828, is a schematic view of a test set-up that was used in a working example for measuring outgassing through an $SiO_x$ barrier coating 348 applied according to the Protocol for Coating Tube Interior with $SiO_x$ on the interior of the wall 346 of a PET tube 358 made according to the Protocol for Forming PET Tube seated with a seal 360 on the upstream end of a Micro-Flow Technology measurement cell generally indicated at 362.

A vacuum pump 364 was connected to the downstream end of a commercially available measurement cell 362 (an Intelligent Gas Leak System with Leak Test Instrument Model ME2, with second generation IMFS sensor, (10μ/min full range), Absolute Pressure Sensor range: 0-10 Torr, Flow measurement uncertainty: +/−5% of reading, at calibrated range, employing the Leak-Tek Program for automatic data acquisition (with PC) and signatures/plots of leak flow vs. time. This equipment is supplied by ATC Inc.), and was configured to draw gas from the interior of the PET vessel 358 in the direction of the arrows through the measurement cell 362 for determination of the mass flow rate outgassed vapor into the vessel 358 from its walls.

The measurement cell 362 shown and described schematically here was understood to work substantially as follows, though this information might deviate somewhat from the operation of the equipment actually used. The cell 362 has a conical passage 368 through which the outgassed flow is directed. The pressure is tapped at two longitudinally spaced lateral bores 370 and 372 along the passage 368 and fed respectively to the chambers 374 and 376 formed in part by the diaphragms 378 and 380. The pressures accumulated in the respective chambers 374 and 376 deflect the respective diaphragms 378 and 380. These deflections are measured in a suitable manner, as by measuring the change in capacitance between conductive surfaces of the diaphragms 378 and 380 and nearby conductive surfaces such as 382 and 384. A bypass 386 can optionally be provided to speed up the initial pump-down by bypassing the measurement cell 362 until the desired vacuum level for carrying out the test is reached.

The PET walls 350 of the vessels used in this test were on the order of 1 mm thick, and the coating 348 was on the order of 20 nm (nanometers) thick. Thus, the wall 350 to coating 348 thickness ratio was on the order of 50,000:1.

To determine the flow rate through the measurement cell 362, including the vessel seal 360, 15 glass vessels substantially identical in size and construction to the vessel 358 were successively seated on the vessel seal 360, pumped down to an internal pressure of 1 Torr, then capacitance data was collected with the measurement cell 362 and converted to an "outgassing" flow rate. The test was carried out two times on each vessel. After the first run, the vacuum was released with nitrogen and the vessels were allowed recovery time to reach equilibrium before proceeding with the second run. Since a glass vessel is believed to have very little outgassing, and is essentially impermeable through its wall, this measurement is understood to be at least predominantly an indication of the amount of leakage of the vessel and connections within the measurement cell 362, and reflects little if any true outgassing or permeation. The results are in Table 2.

The family of plots 390 in FIG. 12 shows the "outgas" flow rate, also in micrograms per minute, of individual tubes corresponding to the second run data in previously-mentioned Table 2. Since the flow rates for the plots do not increase substantially with time, and are much lower than the other flow rates shown, the flow rate is attributed to leakage.

Table 3 and the family of plots 392 in FIG. 12 show similar data for uncoated tubes made according to the Protocol for Forming PET Tube.

This data for uncoated tubes shows much larger flow rates: the increases are attributed to outgas flow of gases captured on or within the inner region of the vessel wall. There is some spread among the vessels, which is indicative of the sensitivity of the test to small differences among the vessels and/or how they are seated on the test apparatus.

Table 4 and the families of plots 394 and 396 in FIG. 12 show similar data for an $SiO_x$ barrier coating 348 applied according to the Protocol for Coating PET Tube Interior with $SiO_x$ on the interior of the wall 346 of a PET tube made according to the Protocol for Forming PET Tube.

The family of curves 394 for the $SiO_x$ coated, injection-molded PET tubes of this example shows that the $SiO_x$ coating acts as a barrier to limit outgassing from the PET vessel walls, since the flow rate is consistently lower in this test than for the uncoated PET tubes. (The $SiO_x$ coating itself is believed to outgas very little.) The separation between the curves 394 for the respective vessels indicates that this test is sensitive enough to distinguish slightly differing barrier efficacy of the $SiO_x$ coatings on different tubes. This spread in the family 394 is attributed mainly to variations in gas tightness among the $SiO_x$ coatings, as opposed to variations in outgassing among the PET vessel walls or variations in seating integrity (which have a much tighter family 392 of curves). The two curves 396 for samples 2 and 4 are outliers, as demonstrated below, and their disparity from other data is believed to show that the $SiO_x$ coatings of these tubes are defective. This shows that the present test can very clearly separate out samples that have been processed differently or damaged.

Figure 13:
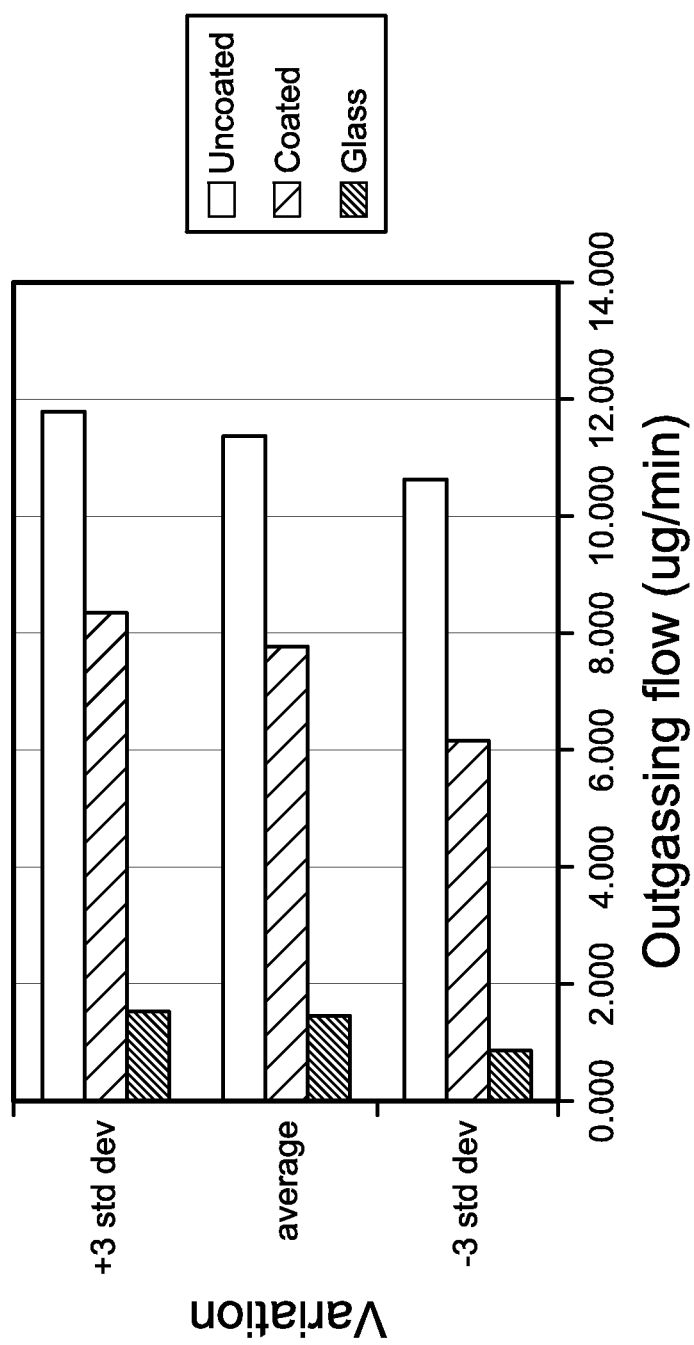
FIG. 13 is a bar graph showing a statistical analysis of the endpoint data shown in FIG. 12.
Figure 14:
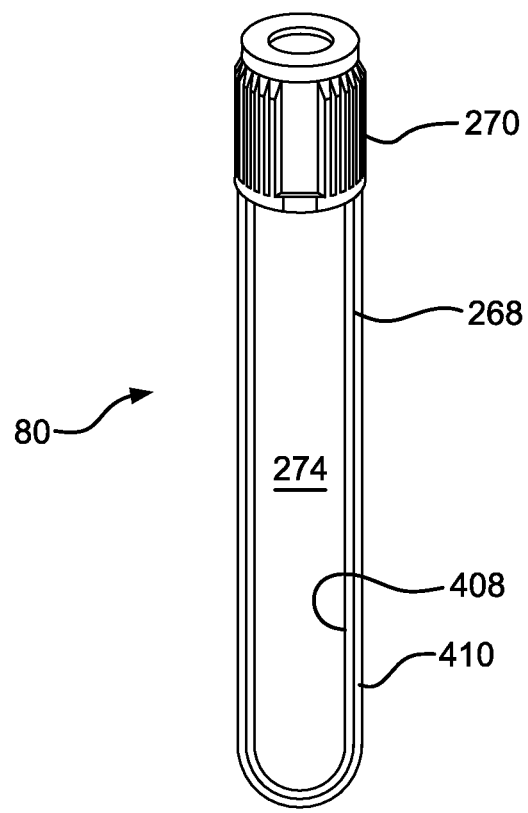
FIG. 14 is a perspective view of a double-walled blood collection tube assembly according to still another embodiment of the disclosure.

Referring to Tables 8 and 9 previously mentioned and FIG. 13, the data was analyzed statistically to find the mean and the values of the first and third standard deviations above and below the mean (average). These values are plotted in FIG. 13.

This statistical analysis first shows that samples 2 and 4 of Table 4 representing coated PET tubes are clear outliers, more than +3 standard deviations away from the mean. These outliers are, however, shown to have some barrier efficacy, as their flow rates are still clearly distinguished from (lower than) those of the uncoated PET tubes.

This statistical analysis also shows the power of an outgassing measurement to very quickly and accurately analyze the barrier efficacy of nano-thickness barrier coatings and to distinguish coated tubes from uncoated tubes (which are believed to be indistinguishable using the human senses at the present coating thickness). Referring to FIG. 13, coated PET vessels showing a level of outgassing three standard deviations above the mean, shown in the top group of bars, have less outgassing than uncoated PET vessels showing a level of outgassing three standard deviations below the mean, shown in the bottom group of bars. This data shows no overlap of the data to a level of certainty exceeding 6σ (six-sigma).

Based on the success of this test, it is contemplated that the presence or absence of an $SiO_x$ coating on these PET vessels can be detected in a much shorter test than this working example, particularly as statistics are generated for a larger number of samples. This is evident, for example from the smooth, clearly separated families of plots even at a time T=12 seconds for samples of 15 vessels, representing a test duration of about one second following the origin at about T=11 seconds.

It is also contemplated, based on this data, that a barrier efficacy for $SiO_x$ coated PET vessels approaching that of glass or equal to glass can be obtained by optimizing the $SiO_x$ coating.

Example 4 (Omitted)

Example 5

Vacuum Retention Study of Tubes Via Accelerated Ageing

Accelerated ageing offers faster assessment of long term shelf-life products. Accelerated ageing of blood tubes for vacuum retention is described in U.S. Pat. No. 5,792,940, Column 1, Lines 11-49.

Three types of polyethylene terephthalate (PET) 13×75 mm (0.85 mm thick walls) molded tubes were tested:

Becton Dickinson Product No. 366703 13×75 mm (no additives) tube (shelf life 545 days or 18 months), closed with Hemogard® system red stopper and uncolored guard [commercial control];

PET tubes made according to the Protocol for Forming PET Tube, closed with the same type of Hemogard® system red stopper and uncolored guard [internal control]; and injection molded PET 13×75 mm tubes, made according to the Protocol for Forming PET Tube, coated according to the Protocol for Coating Tube Interior with $SiO_x$, closed with the same type of Hemogard® system red stopper and uncolored guard [sample].

The BD commercial control was used as received. The internal control and samples were evacuated and capped with the stopper system to provide the desired partial pressure (vacuum) inside the tube after sealing. All samples were placed into a three gallon (3.8 L) 304 SS wide mouth pressure vessel (Sterlitech No. 740340). The pressure vessel was pressurized to 48 psi (3.3 atm, 2482 mm. Hg). Water volume draw change determinations were made by (a) removing 3-5 samples at increasing time intervals, (b) permitting water to draw into the evacuated tubes through a 20 gauge blood collection adaptor from a one liter plastic bottle reservoir, (c) and measuring the mass change before and after water draw.

Results are indicated on Table 5.

The Normalized Average Decay Rate is calculated by dividing the time change in mass by the number of pressurization days and initial mass draw [mass change/(days×initial mass)]. The Accelerated Time to 10% Loss (months) is also calculated. Both data are listed in Table 6.

This data indicates that both the commercial control and uncoated internal control have identical vacuum loss rates, and surprisingly, incorporation of a $SiO_x$ coating on the PET interior walls improves vacuum retention time by a factor of 2.1.

Example 6

Volatile Components from Plasma Coatings ("Outgassing")

COC syringe barrel samples made according to the Protocol for Forming COC Syringe barrel, coated with OMCTS (according to the Protocol for Coating COC Syringe Barrel Interior with OMCTS Lubricity layer) or with HMDSO (according to the Protocol for Coating COC Syringe Barrel Interior with HMDSO Coating) were provided. Outgassing gas chromatography/mass spectroscopy (GC/MS) analysis was used to measure the volatile components released from the OMCTS or HMDSO coatings.

The syringe barrel samples (four COC syringe barrels cut in half lengthwise) were placed in one of the 1½" (37 mm) diameter chambers of a dynamic headspace sampling system (CDS 8400 auto-sampler). Prior to sample analysis, a system blank was analyzed. The sample was analyzed on an Agilent 7890A Gas Chromatograph/Agilent 5975 Mass Spectrometer, using the following parameters, producing the data set out in Table 7:

GC Column: 30 m×0.25 mm DB-5MS (J&W Scientific), 0.25 µm film thickness
Flow rate: 1.0 ml/min, constant flow mode
Detector: Mass Selective Detector (MSD)
Injection Mode: Split injection (10:1 split ratio)
Outgassing Conditions: 1½" (37 mm) Chamber, purge for three hour at 85° C., flow 60 ml/min
Oven temperature: 40° C. (5 min.) to 300° C. @10° C./min.;
hold for 5 min. at 300° C.

The outgassing results from Table 7 clearly indicated a compositional differentiation between the HMDSO-based and OMCTS-based lubricity layers tested. HMDSO-based compositions outgassed trimethylsilanol [$(Me)_3SiOH$] but outgassed no measured higher oligomers containing repeating -$(Me)_2SiO$— moieties, while OMCTS-based compositions outgassed no measured trimethylsilanol [$(Me)_3SiOH$] but outgassed higher oligomers containing repeating -$(Me)_2SiO$— moieties. It is contemplated that this test can be useful for differentiating HMDSO-based coatings from OMCTS-based coatings.

Without limiting the disclosure according to the scope or accuracy of the following theory, it is contemplated that this result can be explained by considering the cyclic structure of OMCTS, with only two methyl groups bonded to each silicon atom, versus the acyclic structure of HMDSO, in which each silicon atom is bonded to three methyl groups. OMCTS is contemplated to react by ring opening to form a diradical having repeating -$(Me)_2SiO$— moieties which are already oligomers, and can condense to form higher oligomers. HMDSO, on the other hand, is contemplated to react by cleaving at one O—Si bond, leaving one fragment containing a single O—Si bond that recondenses as $(Me)_3SiOH$ and the other fragment containing no O—Si bond that recondenses as $[(Me)_3Si]_2$.

The cyclic nature of OMCTS is believed to result in ring opening and condensation of these ring-opened moieties with outgassing of higher MW oligomers (26 ng/test). In contrast, HMDSO-based coatings are believed not to provide any higher oligomers, based on the relatively low-molecular-weight fragments from HMDSO.

Example 7

Density Determination of Plasma Coatings Using X-Ray Reflectivity (XRR)

Sapphire witness samples (0.5×0.5×0.1 cm) were glued to the inner walls of separate PET tubes, made according to the Protocol for Forming PET tubes. The sapphire witness-containing PET tubes were coated with OMCTS or HMDSO (both according to the Protocol for Coating COC Syringe Barrel Interior with OMCTS Lubricity layer, deviating all with 2× power). The coated sapphire samples were then removed and X-ray reflectivity (XRR) data were acquired on a PANalytical X'Pert diffractometer equipped with a parabolic multilayer incident beam monochromator and a parallel plate diffracted beam collimator. A two layer $Si_wO_x$-$C_yH_z$ model was used to determine coating density from the critical angle measurement results. This model is contemplated to offer the best approach to isolate the true $Si_wO_x$-$C_yH_z$ coating. The results are shown in Table 8.

Without limiting the disclosure according to the scope or accuracy of the following theory, it is contemplated that there is a fundamental difference in reaction mechanism in the formation of the respective HMDSO-based and OMCTS-based coatings. HMDSO fragments can more easily nucleate or react to form dense nanoparticles which then deposit on the surface and react further on the surface, whereas OMCTS is much less likely to form dense gas phase nanoparticles. OMCTS reactive species are much more likely to condense on the surface in a form much more similar to the original OMCTS monomer, resulting in an overall less dense coating.

Example 8

Thickness Uniformity of PECVD Applied Coatings

Samples were provided of COC syringe barrels made according to the Protocol for Forming COC Syringe barrel and respectively coated with $SiO_x$ according to the Protocol for Coating COC Syringe Barrel Interior with SiO$_x$ or an OMCTS-based lubricity layer according to the Protocol for Coating COC Syringe Barrel Interior with OMCTS Lubricity layer. Samples were also provided of PET tubes made according to the Protocol for Forming PET Tube, respectively coated and uncoated with SiO$_x$ according to the Protocol for Coating Tube Interior with SiO$_x$ and subjected to an accelerated aging test. Transmission electron microscopy (TEM) was used to measure the thickness of the PECVD-applied coatings on the samples. The previously stated TEM procedure was used. The method and apparatus described by the SiO$_x$ and lubricity layer protocols used in this example demonstrated uniform coating as shown in Table 10.

Example 9

Outgassing Measurement on COC

COC tubes were made according to the Protocol for Forming COC Tube.

Some of the tubes were provided with an interior barrier coating of SiO$_x$ according to the Protocol for Coating Tube Interior with SiO$_x$, and other COC tubes were uncoated. Commercial glass blood collection Becton Dickinson 13×75 mm tubes having similar dimensions were also provided as above. The tubes were stored for about 15 minutes in a room containing ambient air at 45% relative humidity and 70° F. (21° C.), and the following testing was done at the same ambient relative humidity. The tubes were tested for outgassing following the ATC microflow measurement procedure and equipment of Example 3 (an Intelligent Gas Leak System with Leak Test Instrument Model ME2, with second generation IMFS sensor, (10μ/min full range), Absolute Pressure Sensor range: 0-10 Torr, Flow measurement uncertainty: +/−5% of reading, at calibrated range, employing the Leak-Tek Program for automatic data acquisition (with PC) and signatures/plots of leak flow vs. time). In the present case each tube was subjected to a 22-second bulk moisture degassing step at a pressure of 1 mm Hg, was pressurized with nitrogen gas for 2 seconds (to 760 millimeters Hg), then the nitrogen gas was pumped down and the microflow measurement step was carried out for about one minute at 1 millimeter Hg pressure.

Figure 17:
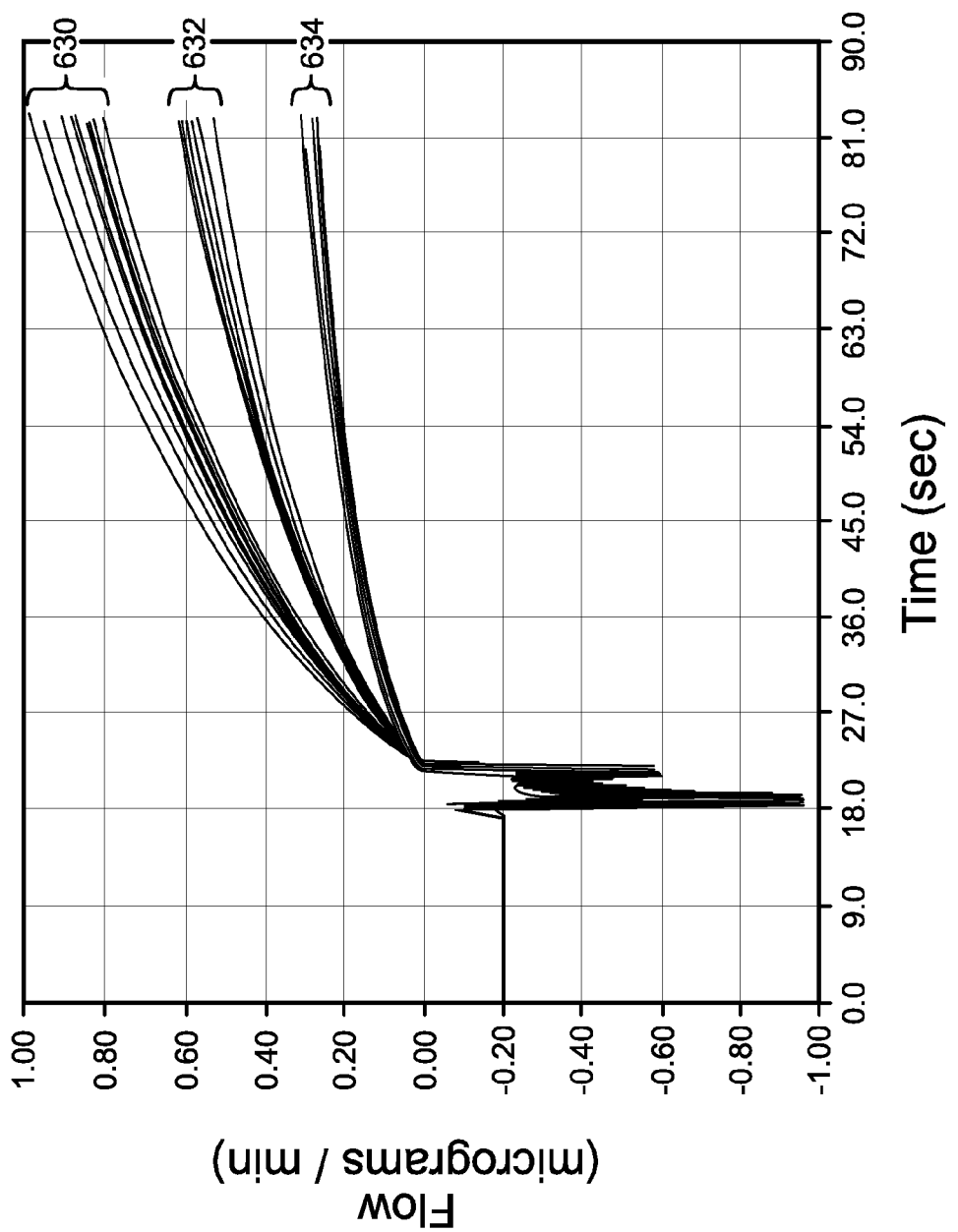
FIG. 17 is a plot of outgassing mass flow rate measured in Example 9.

The result is shown in FIG. 17, which is similar to FIG. 12 generated in Example 3. In FIG. 17, the plots for the uncoated COC tubes are at 630, the plots for the SiO$_x$ coated COC tubes are at 632, and the plots for the glass tubes used as a control are at 634. Again, the outgassing measurement began at about 4 seconds, and a few seconds later the plots 630 for the uncoated COC tubes and the plots 632 for the SiO$_x$ barrier coated tubes clearly diverged, again demonstrating rapid differentiation between barrier coated tubes and uncoated tubes. A consistent separation of uncoated COC (>2 micrograms at 60 seconds) versus SiO$_x$-coated COC (less than 1.6 micrograms at 60 seconds) was realized.

While the disclosure has been illustrated and described in detail in the drawings and foregoing description, such illustration and description are to be considered illustrative or exemplary and not restrictive; the disclosure is not limited to the disclosed embodiments. Other variations to the disclosed embodiments can be understood and effected by those skilled in the art and practising the claimed disclosure, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

TABLE 1

OPTICAL ABSORPTION OF SIO$_x$ COATED PET TUBES (NORMALIZED TO UNCOATED PET TUBE)

| Sample | Coating Time | Average Absorption (@ 615 nm) | Replicates | St. Dev. |
|---|---|---|---|---|
| Reference (uncoated) | — | 0.002-0.014 | 4 | |
| A | 3 sec | 0.021 | 8 | 0.001 |
| B | 2 × 3 sec | 0.027 | 10 | 0.002 |
| C | 3 × 3 sec | 0.033 | 4 | 0.003 |

TABLE 2

FLOW RATE USING GLASS TUBES

| Glass Tube | Run #1 (μg/min.) | Run #2 (μg/min.) | Average (μg/min.) |
|---|---|---|---|
| 1 | 1.391 | 1.453 | 1.422 |
| 2 | 1.437 | 1.243 | 1.34 |
| 3 | 1.468 | 1.151 | 1.3095 |
| 4 | 1.473 | 1.019 | 1.246 |
| 5 | 1.408 | 0.994 | 1.201 |
| 6 | 1.328 | 0.981 | 1.1545 |
| 7 | Broken | Broken | Broken |
| 8 | 1.347 | 0.909 | 1.128 |
| 9 | 1.171 | 0.91 | 1.0405 |
| 10 | 1.321 | 0.946 | 1.1335 |
| 11 | 1.15 | 0.947 | 1.0485 |
| 12 | 1.36 | 1.012 | 1.186 |
| 13 | 1.379 | 0.932 | 1.1555 |
| 14 | 1.311 | 0.893 | 1.102 |
| 15 | 1.264 | 0.928 | 1.096 |
| Average | 1.343 | 1.023 | 1.183 |
| Max | 1.473 | 1.453 | 1.422 |
| Min | 1.15 | 0.893 | 1.0405 |
| Max − Min | 0.323 | 0.56 | 0.3815 |
| Std.. Dev. | 0.097781 | 0.157895 | 0.1115087 |

TABLE 3

FLOW RATE USING PET TUBES

| Uncoated PET | Run #1 (μg/min.) | Run #2 (μg/min.) | Average (μg/min.) |
|---|---|---|---|
| 1 | 10.36 | 10.72 | 10.54 |
| 2 | 11.28 | 11.1 | 11.19 |
| 3 | 11.43 | 11.22 | 11.325 |
| 4 | 11.41 | 11.13 | 11.27 |
| 5 | 11.45 | 11.17 | 11.31 |
| 6 | 11.37 | 11.26 | 11.315 |
| 7 | 11.36 | 11.33 | 11.345 |
| 8 | 11.23 | 11.24 | 11.235 |
| 9 | 11.14 | 11.23 | 11.185 |
| 10 | 11.1 | 11.14 | 11.12 |
| 11 | 11.16 | 11.25 | 11.205 |
| 12 | 11.21 | 11.31 | 11.26 |
| 13 | 11.28 | 11.22 | 11.25 |
| 14 | 10.99 | 11.19 | 11.09 |
| 15 | 11.3 | 11.24 | 11.27 |
| Average | 11.205 | 11.183 | 11.194 |
| Max | 11.45 | 11.33 | 11.345 |
| Min | 10.36 | 10.72 | 10.54 |
| Max − Min | 1.09 | 0.61 | 0.805 |
| Std. Dev. | 0.267578 | 0.142862 | 0.195121 |

TABLE 4

FLOW RATE FOR SiO$_x$ COATED PET TUBES

| Coated PET | Run #1 (μg/min.) | Run #2 (μg/min.) | Average (μg/min.) |
|---|---|---|---|
| 1 | 6.834 | 6.655 | 6.7445 |
| 2 | 9.682 | 9.513 | Outliers |
| 3 | 7.155 | 7.282 | 7.2185 |
| 4 | 8.846 | 8.777 | Outliers |
| 5 | 6.985 | 6.983 | 6.984 |
| 6 | 7.106 | 7.296 | 7.201 |
| 7 | 6.543 | 6.665 | 6.604 |
| 8 | 7.715 | 7.772 | 7.7435 |
| 9 | 6.848 | 6.863 | 6.8555 |
| 10 | 7.205 | 7.322 | 7.2635 |
| 11 | 7.61 | 7.608 | 7.609 |
| 12 | 7.67 | 7.527 | 7.5985 |
| 13 | 7.715 | 7.673 | 7.694 |
| 14 | 7.144 | 7.069 | 7.1065 |
| 15 | 7.33 | 7.24 | 7.285 |
| Average | 7.220 | 7.227 | 7.224 |
| Max | 7.715 | 7.772 | 7.7435 |
| Min | 6.543 | 6.655 | 6.604 |
| Max − Min | 1.172 | 1.117 | 1.1395 |
| Std. Dev. | 0.374267 | 0.366072 | 0.365902 |

TABLE 5

WATER MASS DRAW (GRAMS)

| Tube | \multicolumn{8}{c}{Pressurization Time (days)} |
|---|---|

| Tube | 0 | 27 | 46 | 81 | 108 | 125 | 152 | 231 |
|---|---|---|---|---|---|---|---|---|
| BD PET (commercial control) | 3.0 | | | 1.9 | | | 1.0 | |
| Uncoated PET (internal control) | 4.0 | | | 3.1 | | | 2.7 | |
| SiO$_x$-Coated PET (example) | 4.0 | | | 3.6 | | | 3.3 | |

TABLE 6

CALCULATED NORMALIZED AVERAGE VACUUM DECAY RATE AND TIME TO 10% VACUUM LOSS

| Tube | Normalized Average Decay rate (delta mL/initial mL · da) | Time to 10% Loss (months) - Accelerated |
|---|---|---|
| BDPET (commercial control) | 0.0038 | 0.9 |
| Uncoated PET (internal control) | 0.0038 | 0.9 |
| SiO$_x$-Coated PET (example) | 0.0018 | 1.9 |

TABLE 7

VOLATILE COMPONENTS FROM SYRINGE OUTGASSING

| | Coating Monomer | Me$_3$SiOH (ng/test) | Higher SiOMe oligomers (ng/test) |
|---|---|---|---|
| Uncoated COC syringe - Example | Uncoated | ND | ND |
| HMDSO-based Coated COC syringe- Example | HMDSO | 58 | ND |
| OMCTS- based Coated COC syringe- Example | OMCTS | ND | 26 |

TABLE 8

PLASMA COATING DENSITY FROM XRR DETERMINATION

| Sample | Layer | Density g/cm$^3$ |
|---|---|---|
| HMDSO-based Coated Sapphire - Example | Si$_w$O$_x$C$_y$H$_z$ | 1.21 |
| OMCTS- based Coated Sapphire - Example | Si$_w$O$_x$C$_y$H$_z$ | 1.46 |

TABLE 9

ATOMIC CONCENTRATIONS (IN PERCENT, NORMALIZED TO 100% OF ELEMENTS DETECTED) AND TEM THICKNESS

| Sample | Plasma coating | Si | O | C |
|---|---|---|---|---|
| HMDSO-based Coated COC syringe barrel | Si$_w$O$_x$C$_y$ | 0.76 (22.2%) | 1 (33.4%) | 3.7 (44.4%) |
| OMCTS- based Coated COC syringe barrel | Si$_w$O$_x$C$_y$ | 0.46 (23.6%) | 1 (28%) | 4.0 (48.4%) |
| HMDSO Monomer- calculated | Si$_2$OC$_6$ | 2 (21.8%) | 1 (24.1%) | 6 (54.1%) |
| OMCTS Monomer- calculated | Si$_4$O$_4$C$_8$ | 1 (42%) | 1 (23.2%) | 2 (34.8%) |

TABLE 10

THICKNESS OF PECVD COATINGS BY TEM

| Sample ID | TEM Thickness I | TEM Thickness II | TEM Thickness III |
|---|---|---|---|
| Protocol for Forming COC Syringe Barrel; Protocol for Coating COC Syringe Barrel Interior with SiO$_x$ | 164 nm | 154 nm | 167 nm |
| Protocol for Forming COC Syringe Barrel; Protocol for Coating COC Syringe Barrel Interior with OMCTS Lubricity layer | 55 nm | 48 nm | 52 nm |
| Protocol for Forming PET Tube; Protocol for Coating Tube Interior with SiO$_x$ | 28 nm | 26 nm | 30 nm |
| Protocol for Forming PET Tube (uncoated) | — | — | — |

The invention claimed is:

1. A reflectometry method for detecting discontinuities in a chemical vapor deposition (CVD) coating comprising:
providing a thermoplastic vessel wall having an outside surface, an inside surface, and a CVD coating on at least one of the inside and outside surfaces, the vessel wall and the CVD coating having different indices of refraction;
impinging electromagnetic energy on multiple positions of the CVD coating under conditions effective to cause energy to reflect from the multiple positions of the CVD coating;
analyzing the reflected energy to determine whether the reflected energy includes at least one artifact of a discontinuity in the CVD coating.

2. The method of claim 1, in which the energy source provides energy within at least a portion of the wavelength range from 40 to 1100 nm.

3. The method of claim 1, further comprising mapping the reflected energy to the multiple positions of the CVD coating.

4. The method of claim 3, further comprising recording the map of the reflected energy.

5. The method of claim 4, in which the map is recorded by a charge-coupled device image sensor configured for converting the recorded map to a data stream.

6. The method of claim 1, in which the analyzing step is carried out by a computer processor programmed for analyzing the data stream to find at least one artifact representing a discrete area of the image of contrasting brightness relative to the background of the discrete area, representing a discontinuity.

7. The method of claim 6, in which analyzing comprises determining the area of the discontinuity.

8. The method of claim 6, in which the processor is configured to determine the aggregate area of all discontinuities detected in the CVD coating.

9. The method of claim 1, in which the impinging energy is polychromatic.

10. The method of claim 1, in which the reflected energy contains interference patterns resulting from its interaction with the CVD coating.

11. The method of claim 1, in which the color of the reflected energy differs from the color of the impinging energy.

12. The method of claim 1, in which the vessel wall is at least partially transparent.

13. The method of claim 12, in which the vessel wall is positioned such that the impinging energy passes through the vessel wall to reach the CVD coating.

14. The method of claim 12, in which the vessel wall is positioned such that the reflected energy passes through the vessel wall before the reflected energy is analyzed.

15. The method of claim 12, in which the vessel wall is positioned such that the impinging energy impinges inwardly on the outside of the vessel wall and reflects from a CVD coating positioned on the inside of the vessel wall.

* * * * *